(12) United States Patent
Suematsu et al.

(10) Patent No.: US 11,554,257 B2
(45) Date of Patent: Jan. 17, 2023

(54) MEDICAL DEVICE, EXTRACORPOREAL UNIT, POWER TRANSMISSION SHEET, AND MEDICAL INSTRUMENT

(71) Applicant: FURUKAWA ELECTRIC CO., LTD., Tokyo (JP)

(72) Inventors: Katsuki Suematsu, Tokyo (JP); Takeshi Yagi, Tokyo (JP); Atsushi Himura, Tokyo (JP); Kazutaka Nara, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 17/638,402

(22) PCT Filed: Aug. 24, 2020

(86) PCT No.: PCT/JP2020/031803
§ 371 (c)(1),
(2) Date: Feb. 25, 2022

(87) PCT Pub. No.: WO2021/039705
PCT Pub. Date: Mar. 4, 2021

(65) Prior Publication Data
US 2022/0305247 A1 Sep. 29, 2022

(30) Foreign Application Priority Data
Aug. 29, 2019 (JP) .............................. JP2019-156919

(51) Int. Cl.
*A61M 39/02* (2006.01)
*H02J 50/10* (2016.01)
(Continued)

(52) U.S. Cl.
CPC .... *A61M 39/0208* (2013.01); *A61M 5/14276* (2013.01); *A61M 39/0247* (2013.01);
(Continued)

(58) Field of Classification Search
CPC .............. A61M 39/0208; A61M 39/04; A61M 39/0247; A61M 2039/0205;
(Continued)

(56) References Cited

U.S. PATENT DOCUMENTS

| 5,009,644 A | 4/1991 | McDonald |
| 5,171,228 A | 12/1992 | McDonald |

(Continued)

FOREIGN PATENT DOCUMENTS

| EP | 3 459 585 A1 | 3/2019 |
| JP | 2-191468 A | 7/1990 |

(Continued)

OTHER PUBLICATIONS

International Search report dated Oct. 20, 2020 in PCT/JP2020/031803, filed on Aug. 24, 2020, 3 pages.
(Continued)

*Primary Examiner* — Nathan R Price
*Assistant Examiner* — Anh Bui
(74) *Attorney, Agent, or Firm* — Oblon, McClelland, Maier & Neustadt, L.L.P.

(57) ABSTRACT

A power transmission unit includes a second coil which contactlessly transmits power, a power reception unit includes a first coil that receives the power transmitted from the power transmission unit, and a medical instrument includes the power reception unit and is embedded in a body. The medical instrument includes a notification unit that is composed of a plurality of light emitting units that provides notification that a relative positional relationship between the power transmission unit and the power reception unit has reached a predetermined state by emitting light using the power received at the power reception unit when the predetermined state is reached by the movement of the power transmission unit. A soft unit into which an injection needle (Continued)

is inserted, the plurality of light emitting units being arranged so as to extend along an outer edge of the soft unit.

8 Claims, 31 Drawing Sheets

(51) Int. Cl.
  *A61M 39/04*     (2006.01)
  *A61N 1/378*     (2006.01)
  *A61N 1/372*     (2006.01)
  *H01F 38/14*     (2006.01)
  *H02J 50/90*     (2016.01)
  *A61M 5/142*     (2006.01)

(52) U.S. Cl.
  CPC .......... *A61M 39/04* (2013.01); *A61N 1/3787* (2013.01); *A61N 1/37229* (2013.01); *H01F 38/14* (2013.01); *H02J 50/10* (2016.02); *H02J 50/90* (2016.02); *A61M 2039/0205* (2013.01); *A61M 2039/0238* (2013.01); *A61M 2205/583* (2013.01); *A61M 2205/8243* (2013.01); *H02J 2310/23* (2020.01)

(58) Field of Classification Search
  CPC .... A61M 2039/0238; A61M 2205/583; A61M 2205/8243; A61M 5/14276; A61N 1/3787; A61N 1/37229; H02J 50/10; H02J 50/90; H02J 2310/23; H01F 38/14
  See application file for complete search history.

(56) References Cited

U.S. PATENT DOCUMENTS

| | | |
|---|---|---|
| 5,690,693 A | 11/1997 | Wang et al. |
| 2004/0199220 A1 | 10/2004 | Cantlon |
| 2009/0227863 A1 | 9/2009 | Bzostek et al. |
| 2011/0275930 A1 | 11/2011 | Jho et al. |
| 2015/0028798 A1 | 1/2015 | Dearden et al. |
| 2015/0127069 A1 | 5/2015 | Dearden et al. |
| 2015/0148665 A1 | 5/2015 | Sato |
| 2019/0329015 A1 | 10/2019 | Kang |

FOREIGN PATENT DOCUMENTS

| | | |
|---|---|---|
| JP | 3-90168 A | 4/1991 |
| JP | 11-506646 A | 6/1999 |
| JP | 2013-531999 A | 8/2013 |
| JP | 5958922 B2 | 8/2016 |
| JP | 2016-528974 A | 9/2016 |
| WO | WO 96/40367 A1 | 12/1996 |
| WO | WO 2011/140379 A2 | 11/2011 |
| WO | WO 2015/017474 A2 | 2/2015 |

OTHER PUBLICATIONS

Notice of Reasons for Refusal issued in JP Application No. 2019-156919, dated Apr. 13, 2021, 13 pages (with English Translation).
Notice of Reasons for Refusal issued in JP Application No. 2019-156919, dated Aug. 31, 2021, 5 pages (with English Translation).
Notice of Reasons for Refusal dated Jul. 26, 2022, in Japanese Patent Application No. 2021-210741, with English machine translation, 10 pages.
Extended European Search Report dated Aug. 2, 2022, in European Patent Application No. 20857565.4, citing references 1-3, 9 pages.

MEDICAL DEVICE, EXTRACORPOREAL UNIT, POWER TRANSMISSION SHEET, AND MEDICAL INSTRUMENT

TECHNICAL FIELD

The present disclosure relates to a medical device for detecting a position of an implantable medical instrument for use within the body of a subject, an extracorporeal unit, a power transmission sheet, and the medical instrument.

BACKGROUND ART

A body-implantable medical device in which a body portion of a medical instrument is implanted into a body is used for charging a medicinal solution into the body. This medical instrument reduces the burden on patients who need frequent injections for charging a medicinal solution. Such a medical instrument has a soft portion through which an injection needle is inserted into the body portion. This soft portion is made of, for example, silicone rubber or other materials. With the medical instrument, a medicinal solution is injected into a medicinal solution container through the soft portion. The medicinal solution is transported through a catheter to blood vessels.

In such a medical instrument, since the body portion is implanted in the body, it is difficult to specify the position of the soft portion by way of visual recognition from the outside of the body.

Therefore, a medical instrument is considered which includes a soft portion provided by mixing a luminescent material that emits near-infrared fluorescence by irradiation with near-infrared excitation light with a resin material, by applying the technique proposed in Patent Document 1. In such a medical instrument, there is a possibility of the position of the soft portion being able to be visually specified by converting the near-infrared fluorescence into visible light.

Patent Document 1: Japanese Patent No. 5958922

DISCLOSURE OF THE INVENTION

Problems to be Solved by the Invention

However, when such a luminescent material is mixed with the resin material to constitute a soft portion, there is a possibility of the luminescent material is aggregating and the amount of near-infrared fluorescence emitted by the luminescent material being reduced due to concentration quenching, such that it is difficult to specify the position of the soft portion as a result.

It should be noted that, although a medical instrument having a soft portion has been described here, a similar problem has also occurred in an intracorporeal implantable medical device without a soft portion.

Exemplary embodiments of the present disclosure provide a medical device that makes it possible to easily confirm a predetermined location in an implantable medical instrument for use in a body, an extracorporeal unit, a power transmission sheet, and the medical instrument.

Means for Solving the Problems

An exemplary embodiment of the present invention provides a medical device including: a power transmission unit including a second coil that transmits power in a non-contact manner; a power receiving unit including a first coil that receives the power transmitted from the power transmission unit; and an implantable medical instrument for use in a body, the implantable medical instrument including the power receiving unit, the implantable medical instrument including: a notification unit including a plurality of light emitting units which notify that a relative positional relationship between the power transmission unit and the power receiving unit has reached a predetermined state along with a movement of the power transmission unit, by emitting light using the power received by the power receiving unit; and a soft portion for insertion of an injection needle, in which the plurality of light emitting units is arranged along an outer edge of the soft portion.

Furthermore, in the above medical device, the power receiving unit includes a plurality of power receiving units, and the plurality of light emitting units each emit light using power received by a corresponding one of the plurality of power receiving units connected thereto.

Furthermore, in the above medical device, the plurality of light emitting units share the power receiving unit, and emit light using the power received by the power receiving unit.

Furthermore, in the above medical device, the notification unit includes a first light intensity in a brightest location in a circle having a first radius smaller than an inner diameter of the soft portion, and a second light intensity in a brightest location outside a circle having a second radius larger than the first radius, in which the first light intensity and second light intensity differ from each other.

Furthermore, in the above medical device, the power transmission unit includes a plate-shaped sheet portion, the plate-shaped sheet portion includes a second coil that transmits the power, and has a hole in the second coil for insertion of an injection needle thereinto, and a diameter F of the hole is defined by the following expression: $F<(A-2D)$; herein A indicates a diameter of the soft portion, and D indicates a distance between a center of the soft portion and a center of the second coil when the light emitting unit can emit light.

Furthermore, exemplary embodiments of the present disclosure provide an extracorporeal unit that detects a predetermined location of an implantable medical instrument for use in a body including a power receiving unit that receives power transmitted from outside in a non-contact manner, the extracorporeal unit including a power transmission unit including a second coil that transmits power in a non-contact manner, the power transmission unit includes a plate-shaped sheet portion, the plate-shaped sheet portion includes the second coil that transmits the power, and has a hole in the second coil for insertion of an injection needle thereinto, and a diameter F of the hole is defined by the following expression: $F<(A-2D)$; herein A indicates a diameter of the soft portion, and D indicates a distance between a center of the soft portion and a center of the second coil when the light emitting unit can emit light.

Furthermore, exemplary embodiments of the present disclosure provide a power transmission sheet attachable to and detachable from an extracorporeal unit that detects a predetermined location of an implantable medical instrument for use in a body including a power receiving unit that receives power transmitted from outside in a non-contact manner, the power transmission sheet including a plate-shaped sheet portion, the plate-shaped sheet portion includes a second coil that transmits the power, and has a hole in the second coil for insertion of an injection needle thereinto, and a diameter F of the hole is defined by the following expression: $F<(A-2D)$; herein A indicates a diameter of the soft portion, and D indicates a distance between a center of the soft portion and a center of the second coil when the light emitting unit can emit light.

Furthermore, exemplary embodiments of the present disclosure provide an implantable medical instrument for use in a body, including: a power receiving unit including a first coil that receives power transmitted from a power transmission unit of an extracorporeal unit in a non-contact manner; a notification unit including a plurality of light emitting units which notify that a relative positional relationship between the power transmission unit and the power receiving unit has reached a predetermined state along with a movement of the power transmission unit, by emitting light using the power received by the power receiving unit; and a soft portion for insertion of an injection needle, in which the plurality of light emitting units are arranged along an outer edge of the soft portion.

Effects of the Invention

According to exemplary embodiments of the present disclosure, it is possible to easily confirm a predetermined position in an implantable medical instrument for use in a body.

PREFERRED MODE FOR CARRYING OUT THE INVENTION

Figure 1:
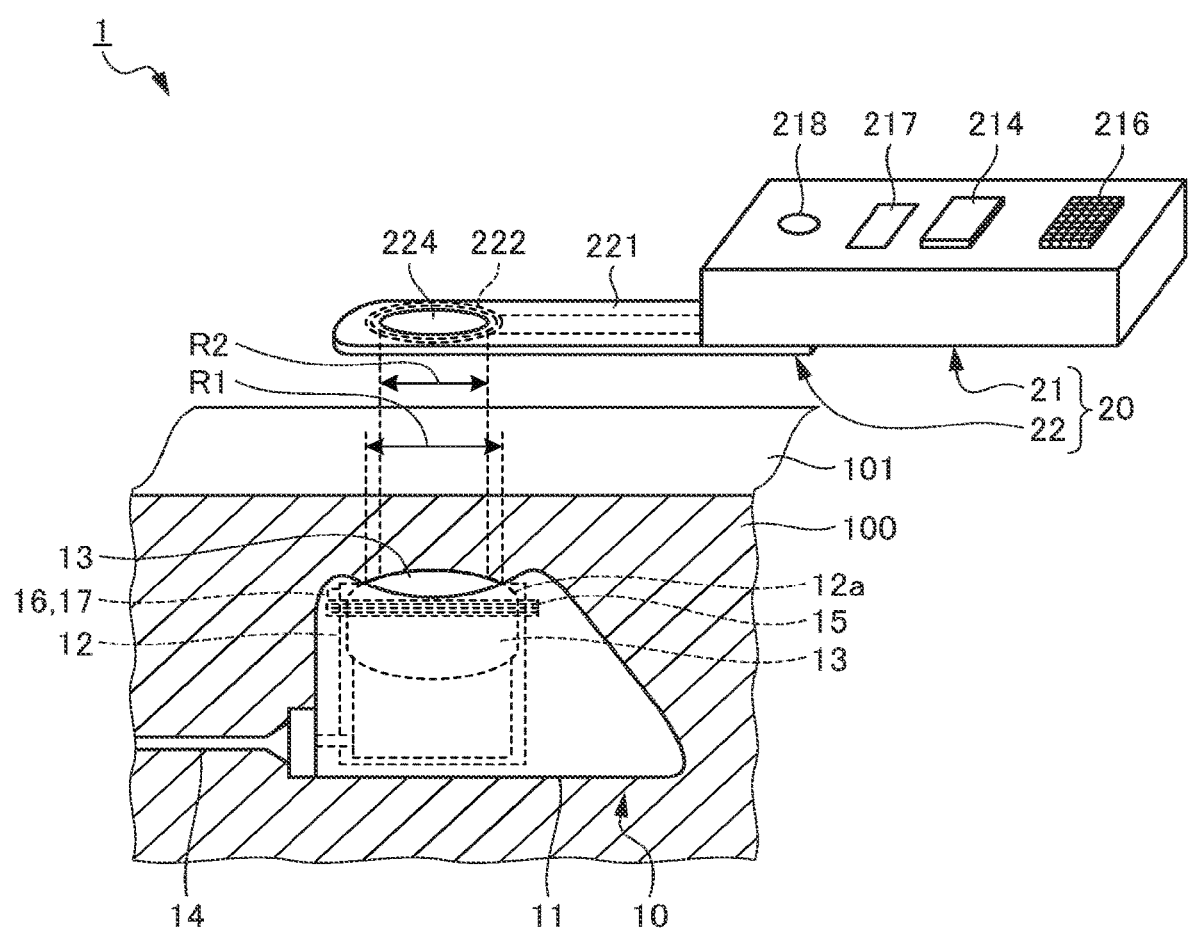
FIG. 1 is a schematic diagram showing a schematic configuration of a medical device according to an exemplary embodiment 1 of the present disclosure.

Hereinafter, exemplary embodiments for carrying out the present disclosure will be described in detail with reference to the accompanying drawings. It should be noted that the present disclosure is not limited to the following exemplary embodiments. In addition, the drawings referred to in the following description are merely schematic representations of the shape, size, and positional relationship to the extent that the content of the present disclosure can be understood. That is, the present disclosure is not limited to the shapes, sizes, and positional relationships illustrated in the drawings. Furthermore, in the following description, configurations and operations of a medical device for detecting a predetermined location in an implantable medical instrument for use in a body of a subject including a human and an animal, an extracorporeal unit, a power transmission sheet, and the medical instrument will be described in detail.

Exemplary Embodiment 1

Configuration of Medical Device

Figure 2:
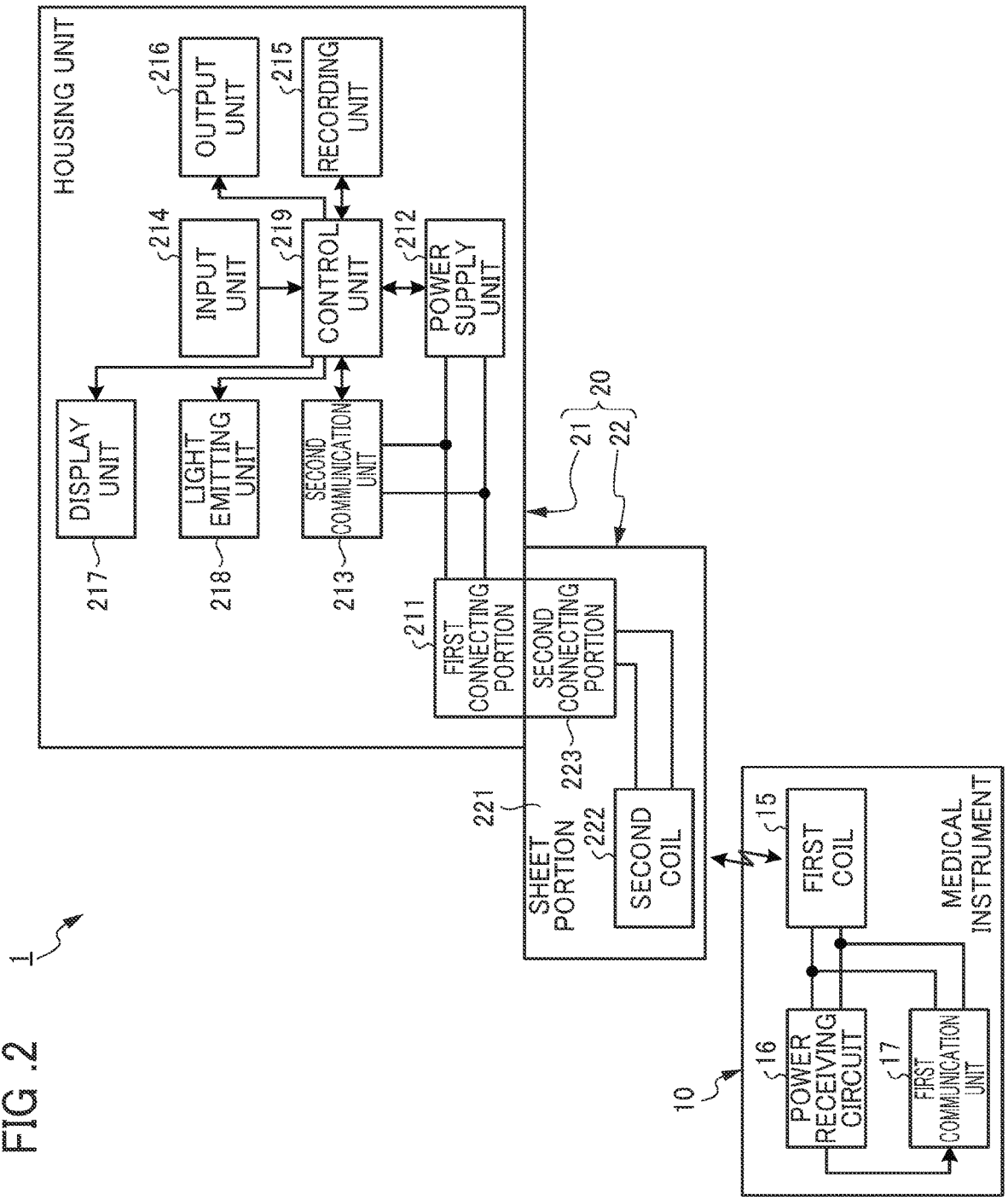
FIG. 2 is a block diagram showing a functional configuration of the medical device according to the exemplary embodiment 1 of the present disclosure.

FIG. 1 is a schematic diagram showing a schematic configuration of a medical device according to an exemplary embodiment 1. FIG. 2 is a block diagram showing a functional configuration of the medical device according to the exemplary embodiment 1. The medical device 1 shown in FIGS. 1 and 2 includes an implantable medical instrument 10 for use in a living body 100 of a subject, and an extracorporeal unit 20 that detects a predetermined location in the medical instrument 10.

Configuration of Medical Instrument

Figure 3:
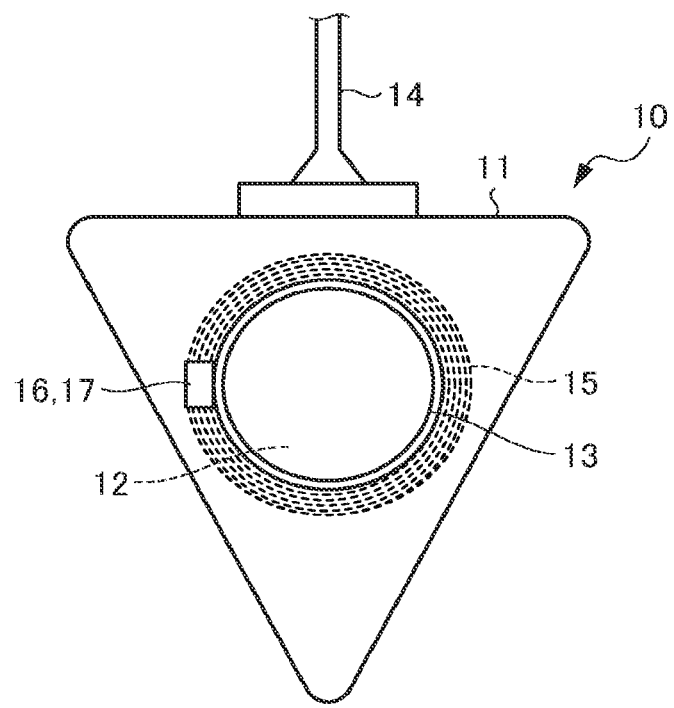
FIG. 3 is a schematic diagram showing a schematic configuration of a medical instrument according to the exemplary embodiment 1 of the present disclosure.

First, a detailed configuration of the medical instrument 10 will be described. FIG. 3 is a schematic diagram showing a schematic configuration of the medical instrument 10.

The medical instrument 10 shown in FIGS. 1, 2 and 3 is, for example, referred to as a subcutaneous implantable port (CV port). As shown in FIGS. 1, 2, and 3, a body portion 11 of the medical instrument 10 is used by implanting in the living body 100.

The body portion 11 is, for example, a housing made of epoxy resin or other materials. As shown in FIGS. 1, 2, and 3, the body portion 11 includes a medicinal solution container 12, a soft portion 13, a catheter 14, a first coil 15, a power receiving circuit 16, and a first communication unit 17.

The medicinal solution container 12 is a chamber for temporarily storing a medicinal solution. The medicinal solution container 12 has an opening 12a having a circular or substantially circular shape on the outside of the body portion 11.

The soft portion 13 is referred to as a septum. The soft portion 13 closes the opening 12a of the medicinal solution container 12. The soft portion 13 is, for example, a soft lid body (silicone diaphragm) made of silicone rubber, and is exposed from the body portion 11 as well. Furthermore, the soft portion 13 has a columnar or substantially columnar shape. The soft portion 13 is a portion through which an injection needle for the injection (infusion) of a medicinal solution can be inserted from a body surface 101 of a subject after the body portion 11 is implanted within the living body 100.

The catheter 14 has one end in communication with the medicinal solution container 12, and the other end for insertion into a blood vessel or the like (not shown). This catheter 14 transports the medicinal solution temporarily stored in the medicinal solution container 12.

The first coil 15 winds a plurality of times in an annular shape on the end surface of the outside of the body portion of the medicinal solution container 12, and thus provided around the soft portion 13. The first coil 15 is small, and mainly constituted by copper wire in order to increase the feeding power; however, for weight reduction, the first coil 15 may be constituted by aluminum wire. For example, the first coil 15 has a weight of about 5 g. The first coil 15 is formed by molding in a manner that is integral with the body portion 11.

The power receiving circuit 16 receives the power generated in the first coil 15 (induced electromotive force), and outputs the received power result of the power to the first communication unit 17. It should be noted that, in the exemplary embodiment 1, the first coil 15 and the power receiving circuit 16 serve as a power receiving unit.

The first communication unit 17 receives the received power result inputted from the power reception circuit 16 via the first coil 15, and transmits a radio wave to the extracorporeal unit 20. It should be noted that the power receiving circuit 16 and the first communication unit 17 may be integrally formed in the IC chip, or may be separately formed. It should be noted that, when a subject implanted with the medical instrument 10 uses MRI, the IC chip may be exposed to a strong magnetic field. Therefore, the medical instrument 10 may include a current detecting function for detecting a current flowing through the first coil 15, and a cut-off function such as a switch for electrically shutting off among the first coil, the power receiving circuit 16, and the first communication unit 17. According to such a configuration, when a large current equal to or greater than a predetermined threshold is detected by the current detection function, it is possible for the IC chip to cut off the current flowing through the first communication unit 17 by electrically cutting off the first coil, the power receiving circuit 16, and the first communication unit 17 by the cut-off function.

Configuration of Extracorporeal Unit

Figure 4:
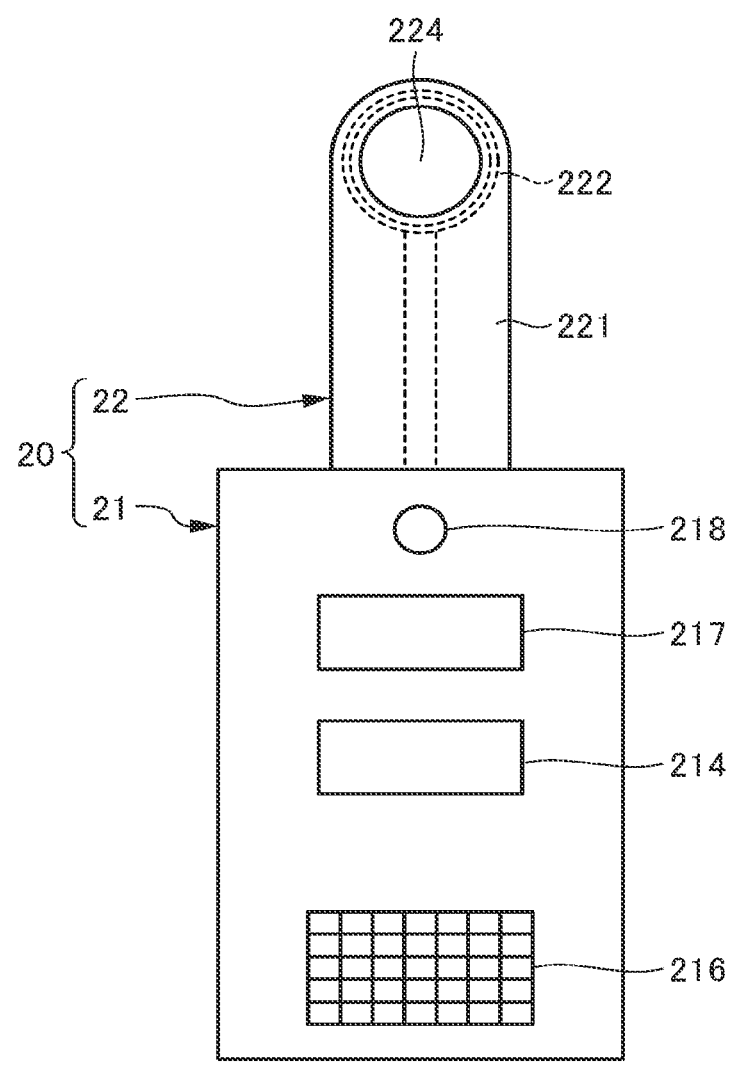
FIG. 4 is a schematic diagram showing a schematic configuration of an extracorporeal unit according to the exemplary embodiment 1 of the present disclosure.

Next, a schematic configuration of the extracorporeal unit 20 will be described. FIG. 4 is a schematic diagram showing a schematic configuration of the extracorporeal unit 20.

The extracorporeal unit 20 shown in FIGS. 1, 2, and 4 detects a predetermined location in the implantable medical instrument 10 for use in the living body 100. When the relative positional relationship between the first coil 15 of the medical instrument 10 and a power transmission unit 22, which will be described later, reaches a predetermined state, the extracorporeal unit 20 notifies that the relative positional relationship between the first coil 15 and the power transmission unit 22, which will be described later, has reached a predetermined state. As shown in FIGS. 1, 2, and 4, the extracorporeal unit 20 includes a housing unit 21 and a power transmission unit 22 attachable and detachable to the housing unit 21. It should be noted that the housing unit 21 and the power transmission unit 22 may be integrally formed. Although details will be described later, as shown in FIG. 1, it is preferable that the inner diameter dimension R2 of a hole 224 is smaller than the outer diameter dimension R1 of the soft portion 13.

Configuration of Housing Unit

First, the configuration of the housing unit 21 will be described. The housing unit 21 houses a circuit board on which, for example, a power supply and IC chips to be described later are mounted. The housing unit 21 supplies power to the power transmission unit 22, and receives the received power result received by the power transmission unit 22. The housing unit 21 includes a first connecting portion 211, a power supply unit 212, a second communication unit 213, an input unit 214, a recording unit 215, an output unit 216, a display unit 217, a light emitting unit 218, and a control unit 219.

The first connecting portion 211 is electrically connectable to the power transmission unit 22 mounted on the housing unit 21, and supplies power inputted from the power supply unit 212 to the power transmission unit 22. The first connecting portion 211 includes, for example, a female electrical coupler.

The power supply unit 212 supplies power to the power transmission unit 22 via the first connecting portion 211 under the control of the control unit 219. The power supply unit 212 includes a battery, a booster circuit, and other components.

The second communication unit 213 outputs the received power result (signal) received by the power transmission unit 22 via the first connecting portion 211 to the control unit 219 under the control of the control unit 219.

The input unit 214 receives an input of an operation by the user. The input unit 214 is implemented by using buttons, switches, a touch panel, and other components. Here, the user refers to any one of a medical doctor, a nurse, a caregiver, and a patient himself/herself as a subject.

The recording unit 215 records various programs and information executed by the extracorporeal unit 20. The recording unit 215 is implemented using volatile memory and nonvolatile memory.

The output unit 216 outputs sound under the control of the control unit 219. The output unit 216 is implemented by using, for example, a speaker or other components.

The display unit 217 displays predetermined information under the control of the control unit 219. The display unit 217 is implemented by using, for example, a liquid crystal or an organic EL (Electro Luminescence).

The light emitting unit 218 emits light under the control of the control unit 219. The light emitting unit 218 is implemented by using LEDs (Light Emitting Diode).

The control unit 219 controls each unit and each portion constituting the extracorporeal unit 20. When the input unit 214 is pressed, the control unit 219 controls the power supply unit 212 to supply power to the power transmission unit 22 via the first connecting portion 211. Furthermore, when the received power result is inputted from the second communication unit 213, the control unit 219 causes the light emitting unit 218 to emit light so as to notify that the relative positional relationship between the power transmission unit 22 and the medical instrument 10 has reached a predetermined state. More specifically, the control unit 219 causes the light emitting unit 218 to emit light so as to notify that the relative positional relationship with the medical instrument 10 has reached a predetermined state, for example, a state in which a second coil 222 of the power transmission unit 22 to be described later is located on the first coil 15 of the medical instrument 10, based on the power of the received power result from the second communication unit 213. The control unit 219 is implemented by using memory and a processor having hardware such as a CPU (Central Processing Unit).

Procedure for Detecting Position of Medical Instrument

Next, the procedure for detecting the position of the medical instrument will be described. The user presses the input unit 214 of the extracorporeal unit 20 so as to supply power from the power supply unit 212 of the housing unit 21 to the second coil 222 of the power transmission unit 22. Then, the user brings the power transmission unit 22 of the extracorporeal unit 20 closer to the medical instrument 10 while searching for the medical instrument 10 embedded in the living body 100. In this case, power is supplied from the power supply unit 212 via a second connecting portion 223 and the first connecting portion 211, whereby the second coil 222 generates a magnetic flux.

Subsequently, the user brings the extracorporeal unit 20 even closer to the medical instrument 10. Under this situation, the light emitting unit 218 notifies the user by emitting light indicating that the relative positional relationship between the first coil 15 of the medical instrument 10 and the second coil 222 has reached a predetermined position in the medical instrument 10. In this case, when the relative positions between the first coil 15 of the medical instrument 10 and the second coil 222 have overlapped each other in the vertical direction, the medical device 1 notifies the user by emitting light. As a result, it is possible for the user to easily confirm the position of the soft portion 13 in the implantable medical instrument 10 for use in the living body 100. More specifically, it is possible for the user to recognize that the soft portion 13 is located below the hole 224 at the position where the light emitting unit 218 emits light.

It should be noted that, when the relative positional relationship between the first coil 15 of the medical instrument 10 and the second coil 222 have reached a predetermined position, the control unit 219 may notify the user by not only causing the light emitting unit 218 to emit light, but also causing the output unit 216 to output sound. Furthermore, the control unit 219 may notify the user by causing the display unit 217 to display information indicating that the second coil 222 has reached the soft portion 13 of the medical instrument 10.

Thereafter, the user inserts the injection needle through the hole 224 provided inside the power transmission unit 22 at a mark provided thereon. Thus, it is possible for the user to insert the injection needle into the soft portion 13 without losing the position of the soft portion 13 of the medical instrument 10, and thus, it is possible to easily inject the medicinal solution into the medicinal solution container 12.

According to the exemplary embodiment 1 described above, when the relative positional relationship between the first coil 15 of the medical instrument 10 and the second coil 222 have reached a predetermined position, the fact that the relative positional relationship between the first coil 15 of the medical instrument 10 and the second coil 222 have reached the predetermined position is notified by causing the light emitting unit 218 to emit light, such that it is possible to easily confirm the position of the soft portion 13 in the implantable medical instrument 10 for use in the living body 100.

Furthermore, according to the exemplary embodiment 1, since the power transmission unit 22 of the extracorporeal unit 20 is attachable to and detachable from the housing unit 21, the housing unit 21 can be used for other subjects, such that the cost of introducing the medical device 1 can be reduced.

Furthermore, according to the exemplary embodiment 1, since the first coil 15 is provided in an annular shape around the soft portion 13, the position (shape) of the soft portion 13 in the medical instrument 10 can be easily confirmed by the light emitting unit 218 emitting light for the notification.

Furthermore, according to the exemplary embodiment 1, since the hole 224 is provided at the center where the second coil 222 of the power transmission unit 22 is provided, it is possible to easily insert the injection needle into the soft portion 13 of the medical instrument 10 in a state in which the relative positional relationship between the first coil 15 of the medical instrument 10 and the second coil 222 have reached a predetermined position.

Exemplary Embodiment 2

Next, exemplary embodiment 2 will be described. In exemplary embodiment 1 described above, the fact that the relative positional relationship between the first coil 15 in the medical instrument 10 and the second coil 222 has reached a predetermined state is notified by the light emitting unit 218 of the extracorporeal unit 20 performing light emission or the like. However, in exemplary embodiment 2, a notification unit is provided in a medical instrument to perform a notification. The same components as those of the medical device 1 according to exemplary embodiment 1 described above are denoted by the same reference numerals, and a detailed description thereof is omitted.

Configuration of Medical Device

Figure 5:
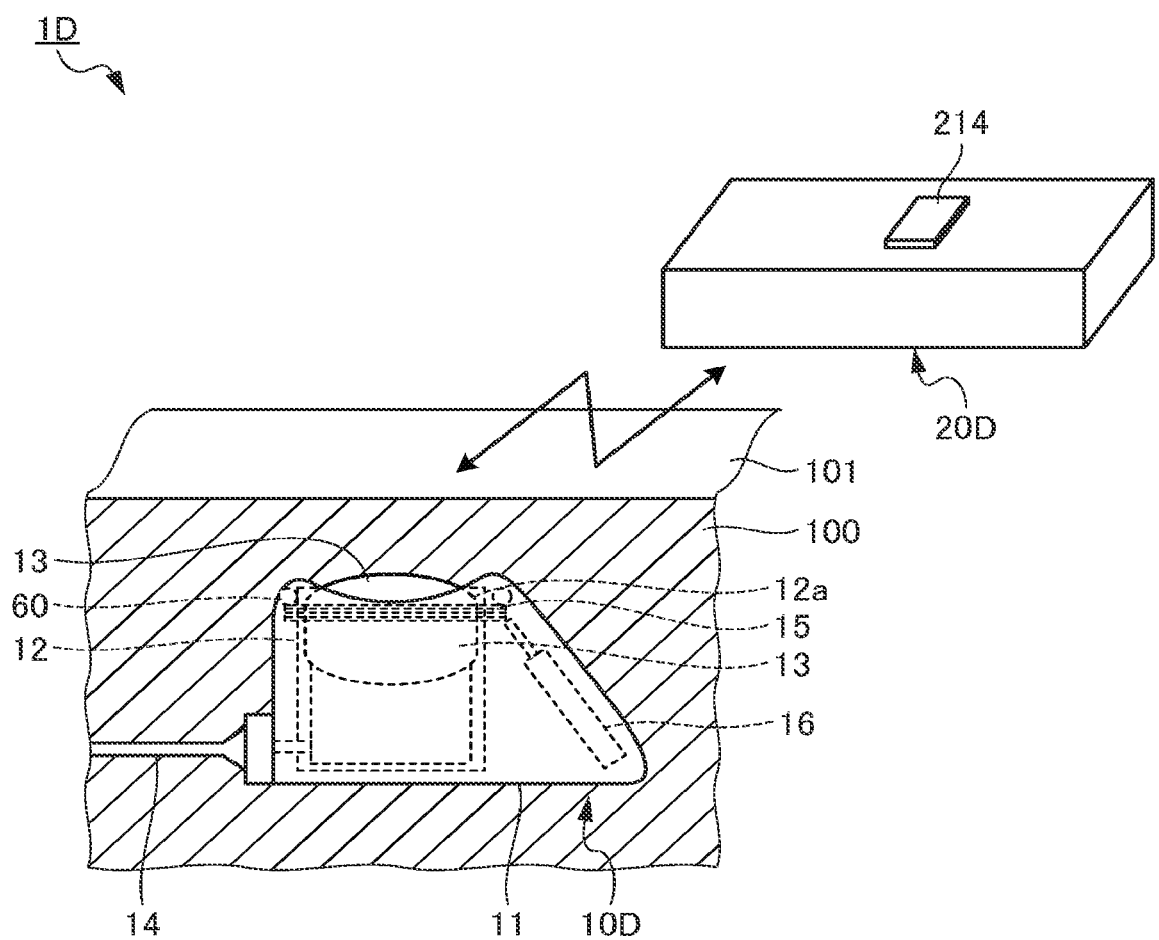
FIG. 5 is a schematic diagram showing a schematic configuration of a medical instrument according to an exemplary embodiment 2 of the present disclosure.
Figure 6:
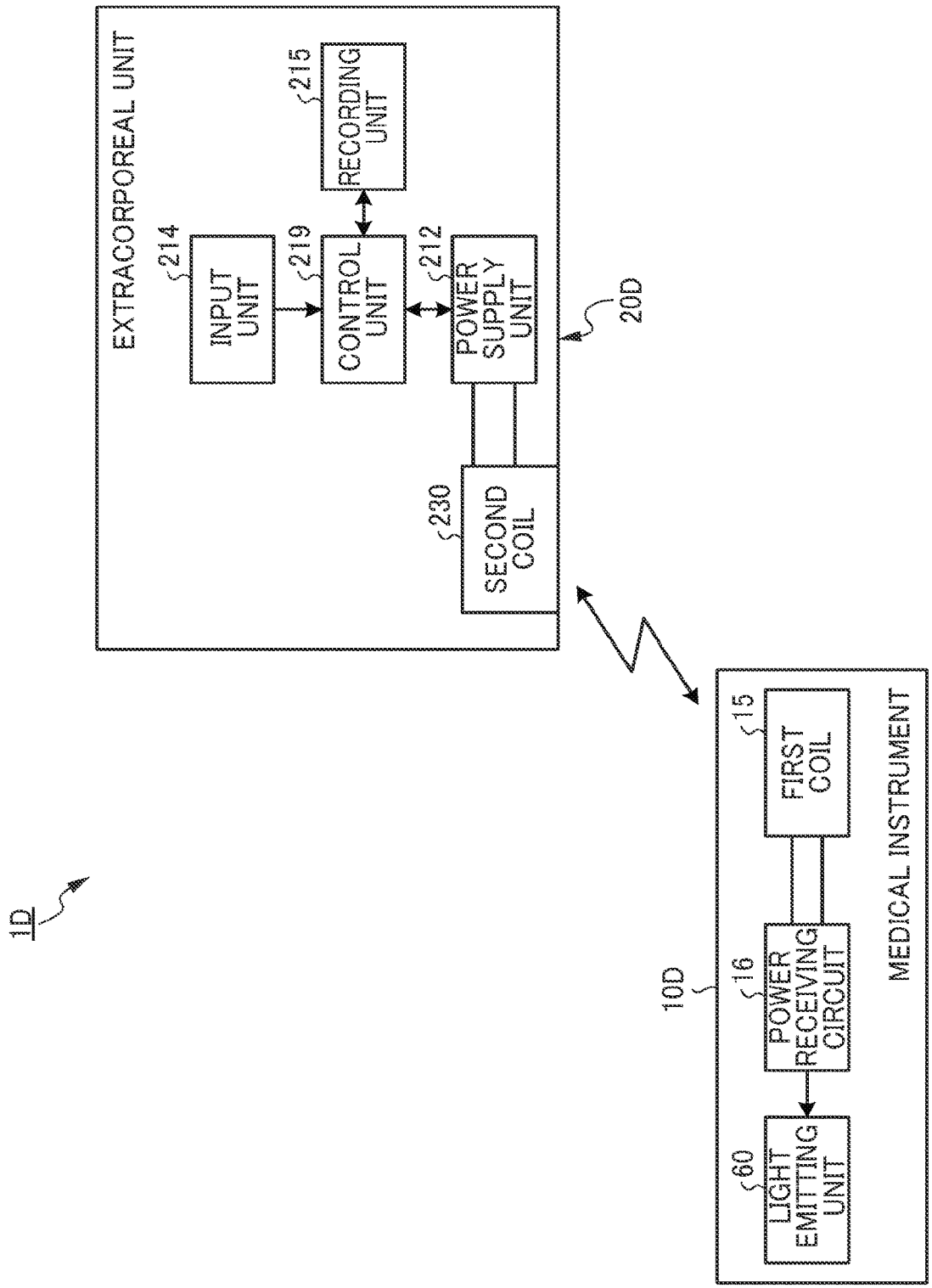
FIG. 6 is a block diagram showing a functional configuration of a medical device according to the exemplary embodiment 2 of the present disclosure.

FIG. 5 is a schematic diagram showing a schematic configuration of a medical instrument according to exemplary embodiment 2. FIG. 6 is a block diagram showing a functional configuration of the medical device according to exemplary embodiment 2.

A medical device 1D shown in FIGS. 5 and 6 includes an implantable medical instrument 10D for use in the living body 100 of a subject, and an extracorporeal unit 20D that detects a predetermined location in the medical instrument 10.

Configuration of Medical Instrument

Figure 7:
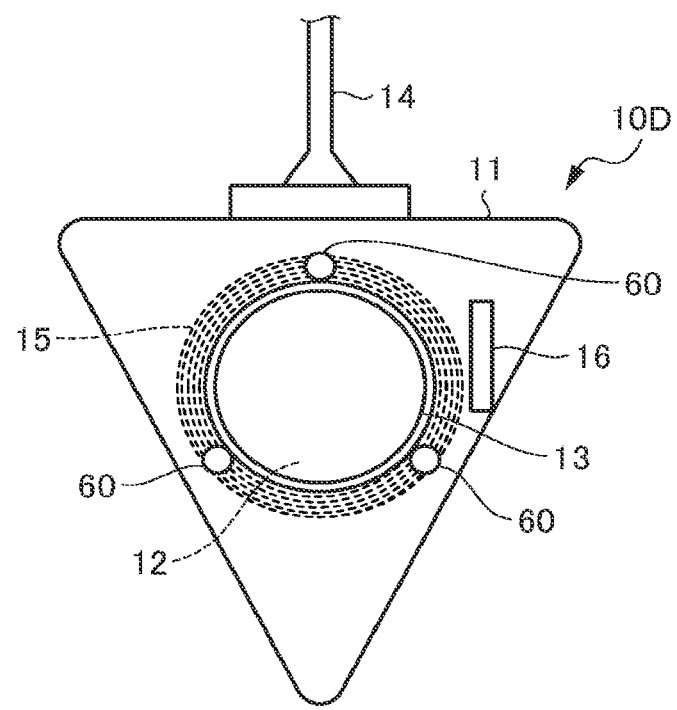
FIG. 7 is a schematic view showing a schematic configuration of the medical instrument according to the exemplary embodiment 2 of the present disclosure.

First, a detailed configuration of the medical instrument 10D will be described. FIG. 7 is a schematic diagram showing a schematic configuration of the medical instrument 10D.

The medical instrument 10D shown in FIGS. 5, 6, and 7 includes a plurality of light emitting units 60 in addition to the configuration of exemplary embodiment 1 described above, and the first communication unit 17 is omitted.

Figure 8:
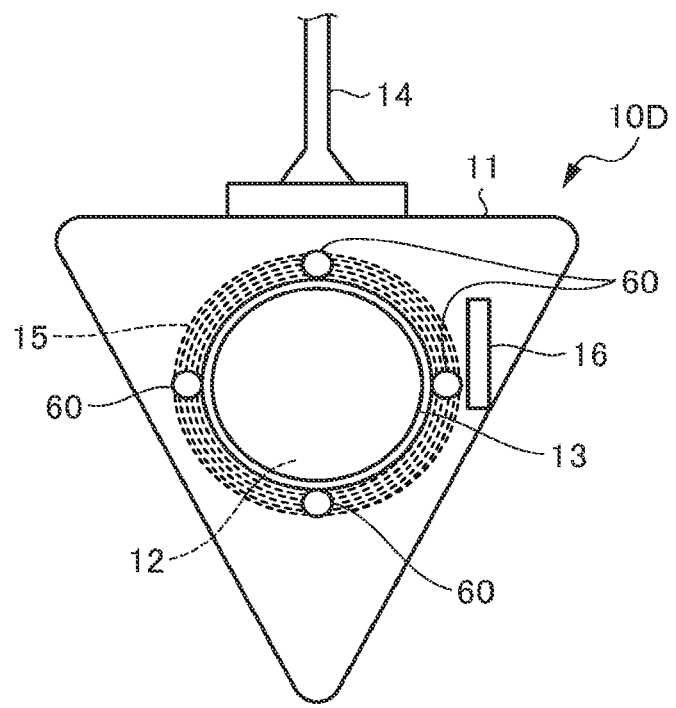
FIG. 8 is a schematic diagram showing a schematic configuration of another medical instrument according to the exemplary embodiment 2 of the present disclosure.

The light emitting units 60 are arranged in an annular or substantially annular shape at predetermined intervals around the soft portion 13. More specifically, the light emitting units 60 are disposed at three positions around the soft portion 13 in an annular or substantially annular shape every 120 degrees in the middle of the first coil 15. The light emitting units 60 each emit light according to the power received by the power receiving circuit 16D. The light emitting units 60 each include an LED. More specifically, it is preferable for the light emitting unit 60 to use an LED having high directivity. More specifically, it is preferable that the light emitting units 60 each use a red LED that emits light in a red wavelength band when transmitting through a living body such as a subject. As shown in FIG. 8, the number and arrangement of the light emitting units 60 can be changed as appropriate.

Configuration of Extracorporeal Unit

Next, the configuration of the extracorporeal unit 20D will be described. In the extracorporeal unit 20D shown in FIGS. 5 and 6, the second communication unit 213, the output unit 216, the display unit 217, and the light emitting unit 218 are omitted from the configuration of the housing unit 21 of exemplary embodiment 1 described above. Furthermore, the extracorporeal unit 20D further includes a second coil 230.

The second coil 230 has an annular or substantially annular shape, generates a magnetic flux in response to the power inputted from the power supply unit 212, and transmits power to the first coil. Furthermore, the power supplied by the second coil 230 allows the light emitting unit 60 to emit light when a predetermined distance between the second coil 230 and the first coil 15 is provided, for example, even when a distance of about several tens of cm is provided therebetween.

The medical device 1D configured as described above supplies electric power from the extracorporeal unit 20D, and the plurality of light emitting units 60 in the medical instrument 10D emit light, thereby notifying the location where the medical instrument 10D is implanted. Thus, it is possible for the user to intuitively grasp the position and the center of the soft portion 13 in the medical instrument 10D from the outside of the subject.

According to exemplary embodiment 2 described above, since the plurality of light emitting units 60 in the medical instrument 10D emit light to notify the position, the position of the soft portion 13 in the medical instrument 10D can be intuitively grasped from the outside of the subject.

Exemplary Embodiment 3

Next, Embodiment 3 will be described. Similar to exemplary embodiment 2 described above, the notification is performed by providing a notification unit in the medical instrument. Furthermore, in the medical instrument 10D according to exemplary embodiment 2, the first coil 15 is disposed around the soft portion 13; however, in the medical instrument 10G according to exemplary embodiment 3, a first coil 15 is disposed for one light emitting unit 60, or first coils 15 are provided for respective light emitting units 60. The same components as those of the medical device 1 according to exemplary embodiment 1 and the medical instrument 10D according to exemplary embodiment 2 described above are denoted by the same reference numerals, and detailed descriptions thereof are omitted.

Configuration of Medical Device

Figure 9:
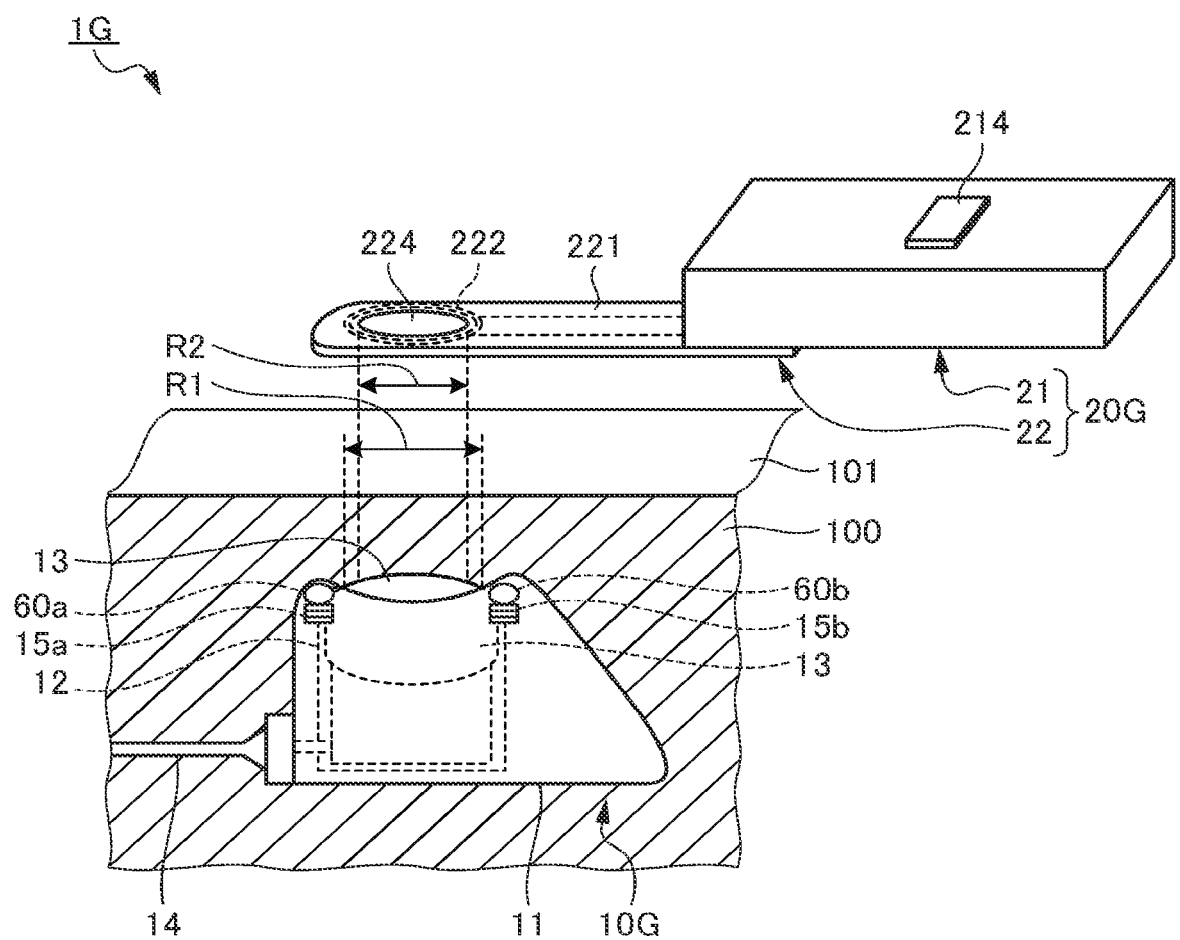
FIG. 9 is a schematic diagram showing a schematic configuration of a medical device according to an exemplary embodiment 3 of the present disclosure.
Figure 10:
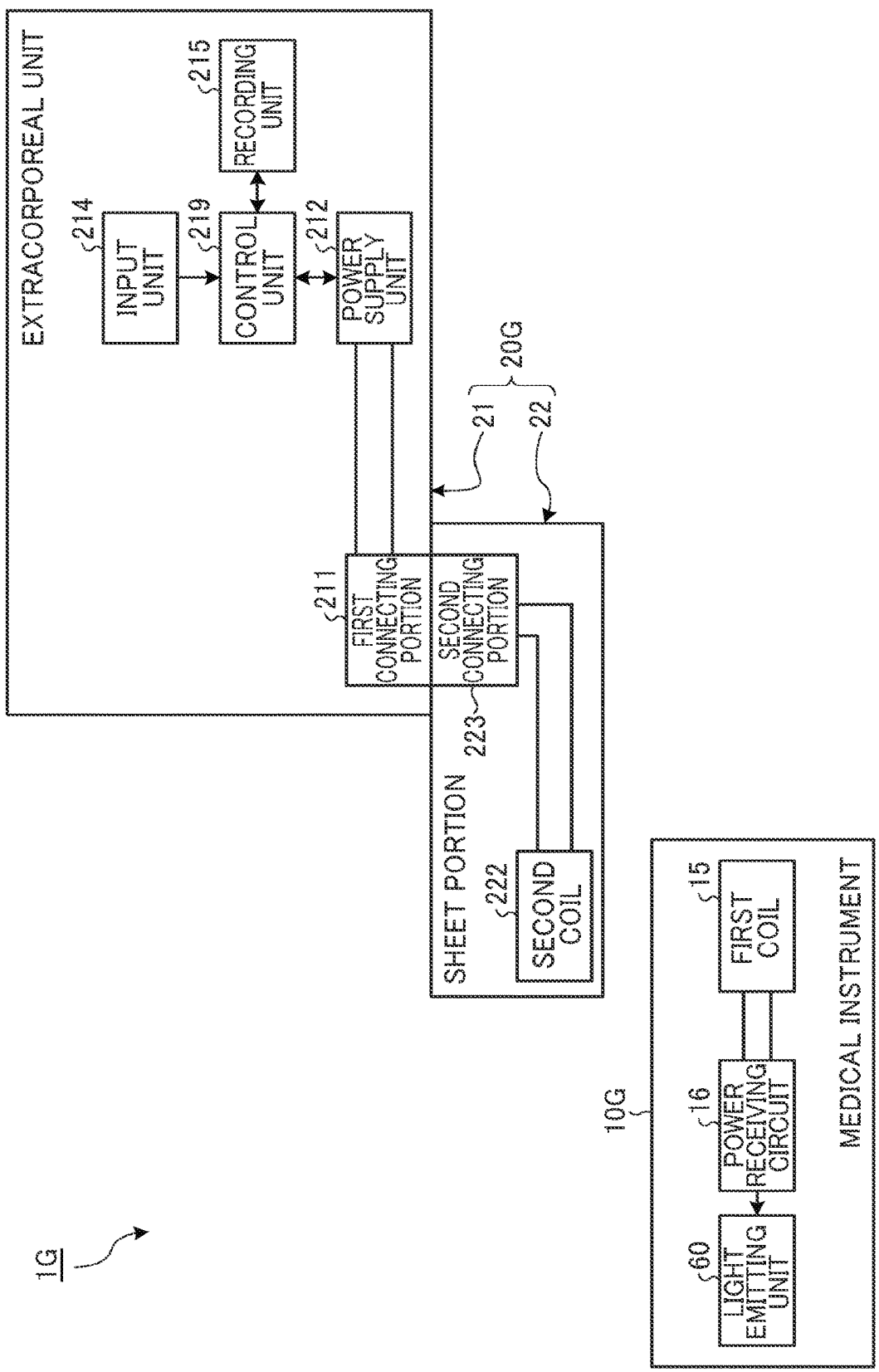
FIG. 10 is a block diagram showing a functional configuration of a medical device according to the exemplary embodiment 3 of the present disclosure.

FIG. 9 is a schematic diagram showing a schematic configuration of a medical device according to exemplary embodiment 3. FIG. 10 is a block diagram showing the functional configuration of the medical device according to exemplary embodiment 3.

A medical device 1G shown in FIGS. 9 and 10 includes an implantable medical instrument 10G for use in a living body 100 of a subject, and an extracorporeal unit 20G that detects a predetermined location in the medical instrument 10G. It should be noted that, although the light emitting units 60 include the light emitting units 60a, 60b, and 60c, this is not limitative. Details thereof will be described later. Furthermore, the first coil 15 includes the first coils 15a, 15b, and 15c; however, this is not limitative.

As shown in FIG. 9, the extracorporeal unit 20G includes a housing unit 21, and a power transmission unit 22 which is attachable to and detachable from the housing unit 21. It should be noted that, in the present embodiment, the concept of "power transmission unit" encompasses a "power transmission sheet". The housing unit 21 and the power transmission unit 22 are connected to each other in a wired or wireless manner. In a case of a wired manner, it is considered that they are connected by a cable of a predetermined length to supply power from the housing unit 21 to the power transmission unit 22. Furthermore, in a case of a wireless manner, it is considered that a non-contact power supply is used to supply power from the housing unit 21 to the power transmission unit 22, for example.

Configuration of Medical Instrument

Figure 11:
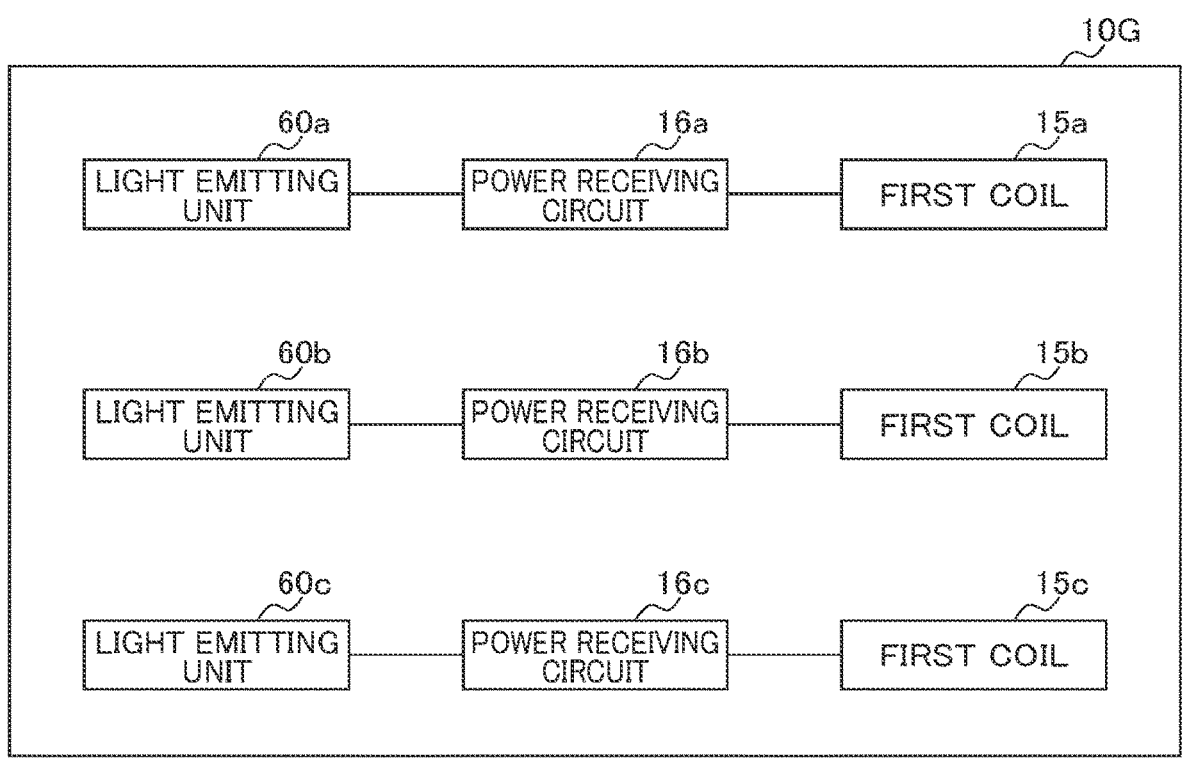
FIG. 11 is a block diagram showing a functional configuration of the medical instrument.
Figure 12:
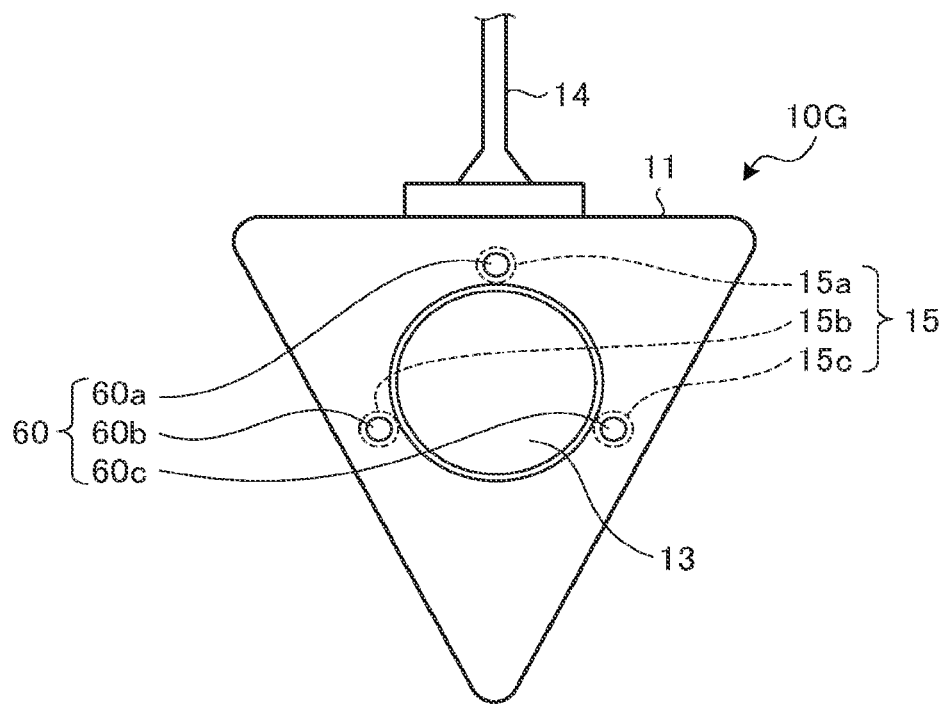
FIG. 12 is a schematic diagram showing a schematic configuration of a medical instrument.

First, a detailed configuration of the medical instrument 10G will be described. FIG. 11 is a block diagram showing a functional configuration of the medical instrument 10G. FIG. 12 is a schematic diagram showing a schematic configuration of the medical instrument 10G.

The medical device 1G includes the power transmission unit 22, the power receiving unit, and the medical instrument 10G. The power transmission unit 22 includes the second coil 222 that transmits power in a non-contact manner.

The power receiving unit includes the first coil 15 and the power receiving circuit 16. The first coil 15 receives power transmitted from the power transmission unit 22. The power receiving circuit 16 transmits the power received by the first coil 15 (induced electromotive force) to the notification unit. It should be noted that the notification unit is implemented by, for example, the light emitting unit 60, which will be described later. Furthermore, the power receiving circuit 16 converts the power received by the first coil 15 to a predetermined power, and transmits the converted power to the notification unit.

The medical instrument 10G includes the power receiving unit, and is implanted in a body. More specifically, the medical instrument 10G includes the notification unit and the soft portion 13. The notification unit includes a plurality of light emitting units 60 which notify that the relative positional relationship between the power transmission unit 22 and the power receiving unit has reached a predetermined state along with the movement of the power transmission unit 22, by emitting light using the power received by the power receiving unit. The plurality of light emitting units 60 are arranged along the outer edge of the soft portion 13. For example, the plurality of light emitting units 60 are arranged at predetermined intervals along the outer edge of the soft portion 13. An injection needle for injecting a medicinal solution is used for insertion into the soft portion 13.

It should be noted that, in exemplary embodiment 3, three light emitting units 60 are arranged at predetermined intervals (e.g., every 120 degrees) around the soft portion 13; however, the number of light emitting units 60 may be two or may be four or more.

Here, the configuration of the power receiving unit will be described. The power receiving unit includes a plurality of power receiving units. The plurality of light emitting units 60 each emit light using the power received by the power receiving unit connected thereto.

FIG. 11 shows a configuration example including three sets each including a light emitting unit 60, a first coil 15, and a power receiving circuit 16. FIG. 12 is a diagram showing a schematic appearance of the medical instrument 10G.

More specifically, as shown in FIG. 11, the medical instrument 10G includes first coils 15a, 15b, and 15c, power receiving circuits 16a, 16b, and 16c, and light emitting units 60a, 60b, and 60c. It should be noted that, in the following, the "first coil 15" may refer to one among the individual first coils 15a, 15b, and 15c, or alternatively may refer to a concept collectively referring to the first coils 15a, 15b, and 15c. Similarly, the "power receiving circuit 16" may refer to one among the individual power receiving circuits 16a, 16b, and 16c, or alternatively may refer to a concept collectively referring to the power receiving circuits 16a, 16b, and 16c. Similarly, the "light emitting unit 60" may refer to one among the individual light emitting units 60a, 60b, and 60c, or alternatively may refer to a concept collectively referring to the light emitting units 60a, 60b, and 60c.

The first coil 15a supplies the received power to the light emitting unit 60a via the power receiving circuit 16a. The first coil 15b supplies the received power to the light emitting unit 60b via the power receiving circuit 16b. The first coil 15c supplies the received power to the light emitting unit 60c via the power receiving circuit 16c.

Figure 13:
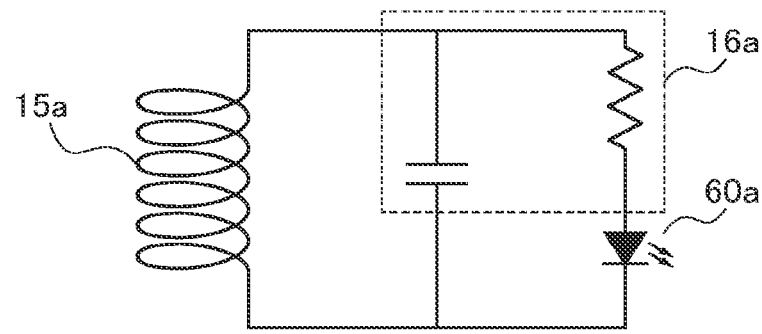
FIG. 13 is a circuit diagram of a power receiving unit including a first coil, a power receiving circuit, and a light emitting unit.

FIG. 13 shows a circuit diagram of the power receiving unit. It should be noted that FIG. 13 shows a configuration of a set including the light emitting unit 60a, the first coil 15a, and the power receiving circuit 16a.

In the case of such a configuration, the light emitting units 60a, 60b, and 60c can emit light independently of each other, and the power receiving unit can be manufactured without depending on the size or shape of the outer diameter of the soft portion 13.

Figure 14:
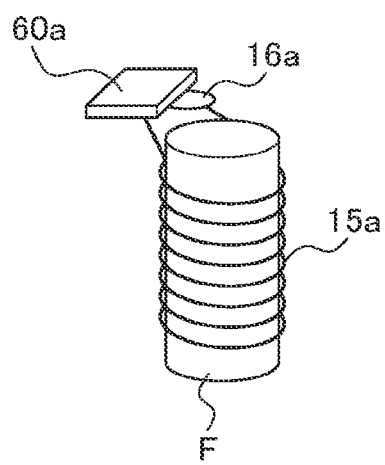
FIG. 14 is a diagram schematically showing the configuration of the power receiving unit.

FIG. 14 is a diagram showing a specific configuration of the power receiving unit. The first coil 15a for transmitting power to the light emitting unit 60a may be wound on the cylindrical iron core F with a small diameter. Since the power receiving unit is integrated in this manner, it can be disposed at any position outside of the medicinal solution container 12. Furthermore, since the power receiving unit includes a configuration in which one coil is provided in one light emitting unit, it is possible to further increase the received power by increasing the number of turns of the coil within the range that can be accommodated in the body outer shape, and it is possible to improve the light emission, leading to enhanced visual recognition. Furthermore, it is preferable that the cylindrical coil has a diameter of 2 mm or less and a height of 5 mm or less.

Next, another configuration of the power receiving unit will be described. A plurality of light emitting units 60 share the power receiving unit, and emit light using the power received by the power receiving unit.

Figure 15:
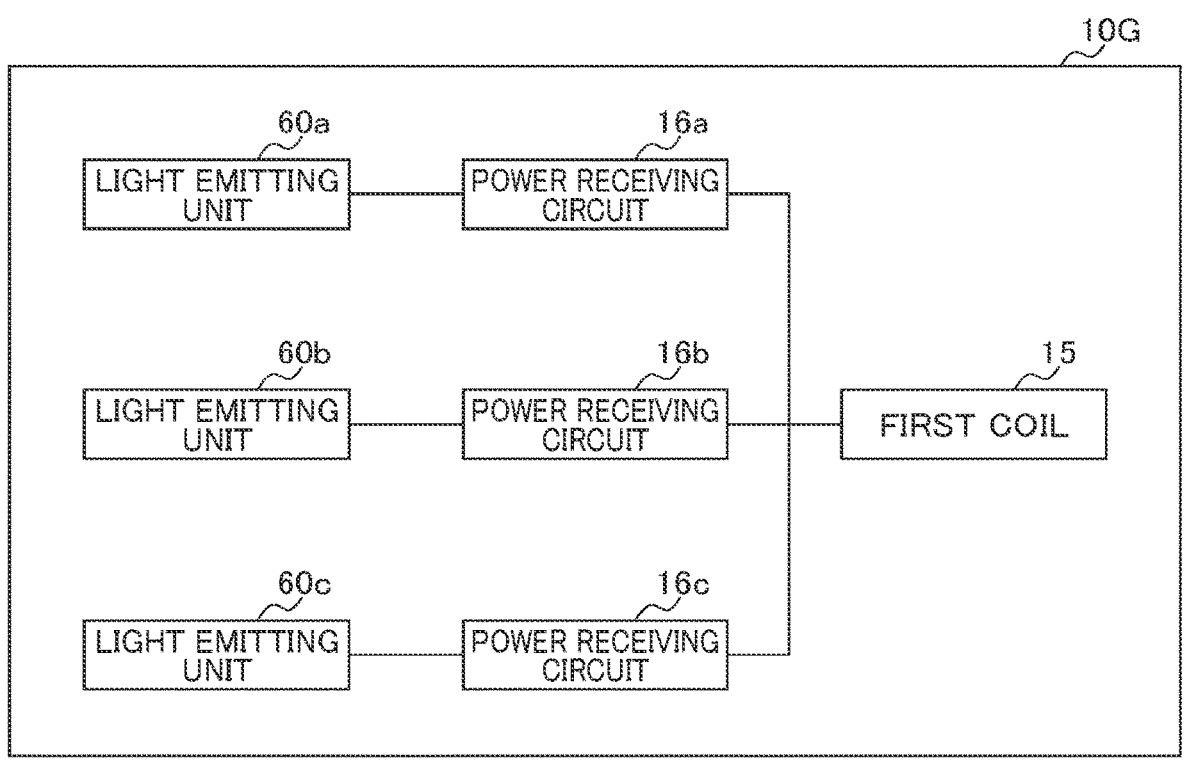
FIG. 15 is a diagram showing a configuration of the power receiving unit in a case of sharing the first coil.
Figure 16:
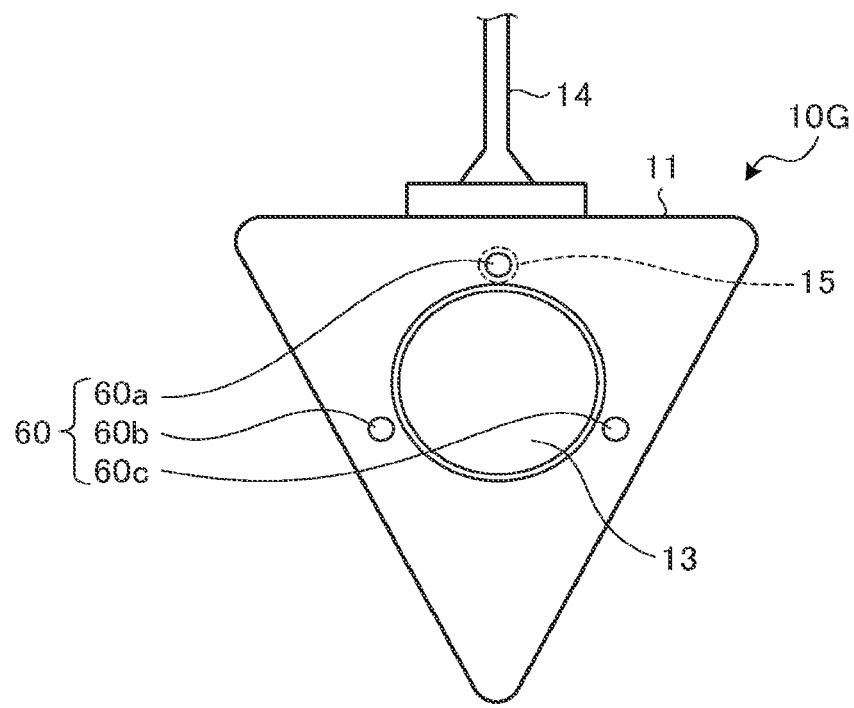
FIG. 16 is a diagram showing a schematic appearance of a medical instrument.
Figure 17:
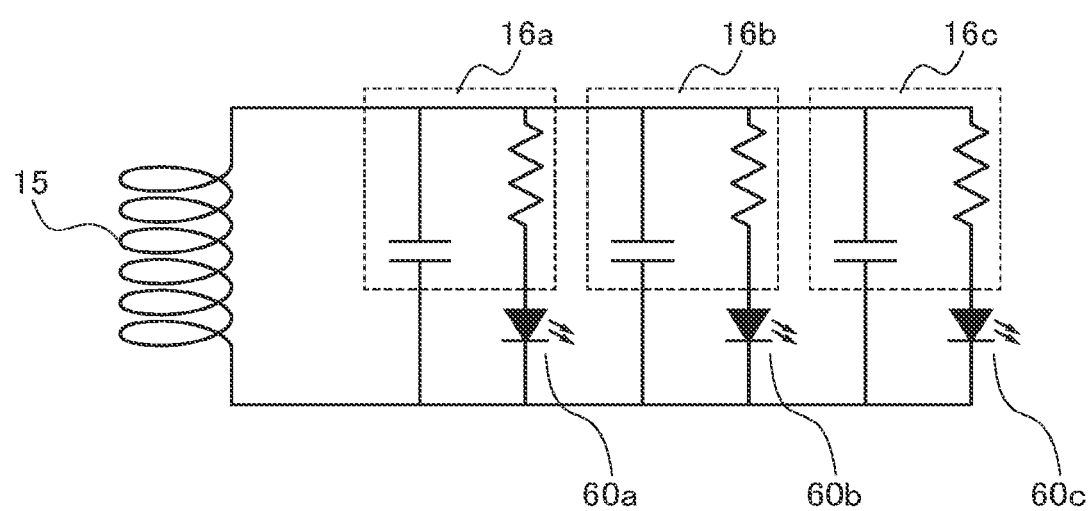
FIG. 17 is a circuit diagram in a case in which the power receiving unit includes one first coil and three light emitting units.

FIG. 15 is a diagram showing a configuration in which the power receiving unit includes one first coil 15, three light emitting units 60a, 60b, and 60c, and three power receiving circuit 16a, 16b, and 16c. FIG. 16 is a diagram showing a schematic appearance of the medical instrument 10G. FIG. 17 is a circuit diagram in a case in which the power receiving unit includes one first coil 15, three light emitting units 60a, 60b, and 60c, and three power receiving circuits 16a, 16b, and 16c.

More specifically, as shown in FIG. 17, the medical instrument 10G includes the first coil 15, the power receiving circuits 16a, 16b, and 16c, and the light emitting units 60a, 60b, and 60c. It should be noted that the power receiving circuit 16 may include a single capacitor, and may be shared by the light emitting unit 60a, 60b, and 60c.

In other words, the power receiving circuit 16a, 16b, and 16c, and the light emitting unit 60a, 60b, and 60c may share the first coil 15.

FIG. 17 shows a circuit diagram in a case in which the power receiving unit includes the first coil 15 and three light emitting units 60. A pair of the power receiving circuit 16a and the light emitting unit 60a, a pair of the power receiving circuit 16b and the light emitting unit 60b, and a pair of the power receiving circuit 16c and the light emitting unit 60c, are connected to the first coil 15 in parallel.

In the case of such a configuration, the light emitting units 60a, 60b, and 60c can emit light at the same time, and the power receiving unit can be manufactured without depending on the size or shape of the outer diameter of the soft portion 13.

It should be noted that FIG. 16 shows a configuration in which the first coil 15 is installed in an annular or substantially annular shape only around the light emitting unit 60a; however, the present invention is not limited to this configuration, and may be installed in an annular or substantially annular shape around the soft portion 13 as shown in FIG. 7.

Next, a specific configuration of the notification unit will be described. The notification unit includes a first light intensity in the brightest location in a circle having a first radius smaller than the inner diameter of the soft portion 13, and a second light intensity in the brightest location outside the circle having a second radius larger than the first radius, and the first and second light intensities differ from each other.

Figure 18:
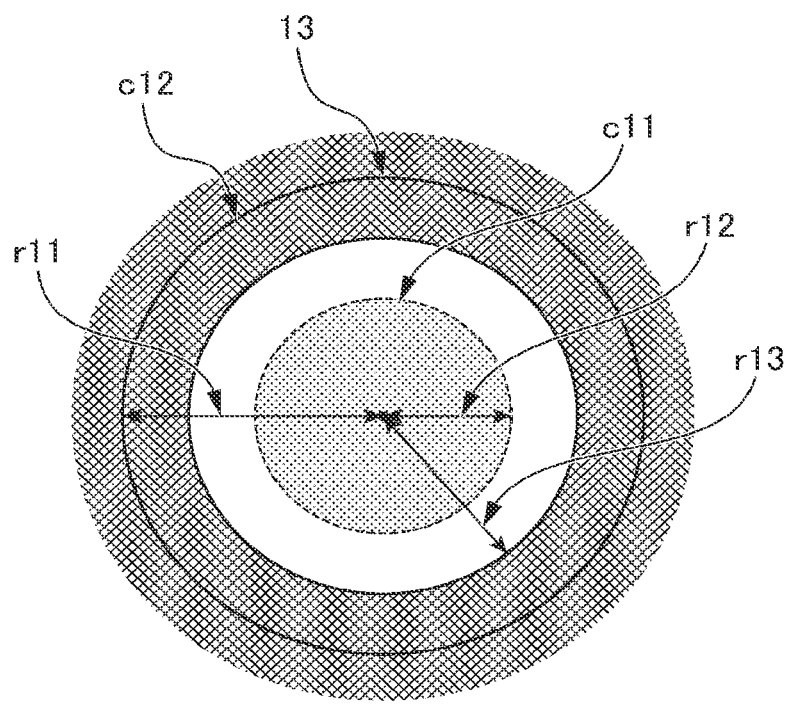
FIG. 18 is a diagram for explaining a case in which a first light intensity and a second light intensity have a first relationship.

FIG. 18 is a diagram for explaining a case in which the first light intensity and the second light intensity have a first relationship. The first relationship refers to "first light intensity">"second light intensity". r11 represents the inner diameter of the soft portion 13. r12 represents a first radius smaller than the inner diameter of the soft portion 13. r13 represents a second radius larger than the first radius. c11 represents an inner circle having the first radius r12. c12 represents an outer circle having a second radius r13.

Furthermore, the brightest location in the inner circle c11 having the first radius r12 refers to, for example, the vicinity of the center of the inner circle c11. The brightest location in the outer circle c12 having the second radius r13 refers to, for example, the vicinity of the circumference of the outer circle c12.

That is, the vicinity of the center of the inner circle c11 appears brighter than the vicinity of the circumference of the outer circle c12. In this manner, the notification unit can emit light differently to show the difference between the first light intensity and the second light intensity, whereby it is possible to notify the location near the center of the soft portion 13.

Figure 19:
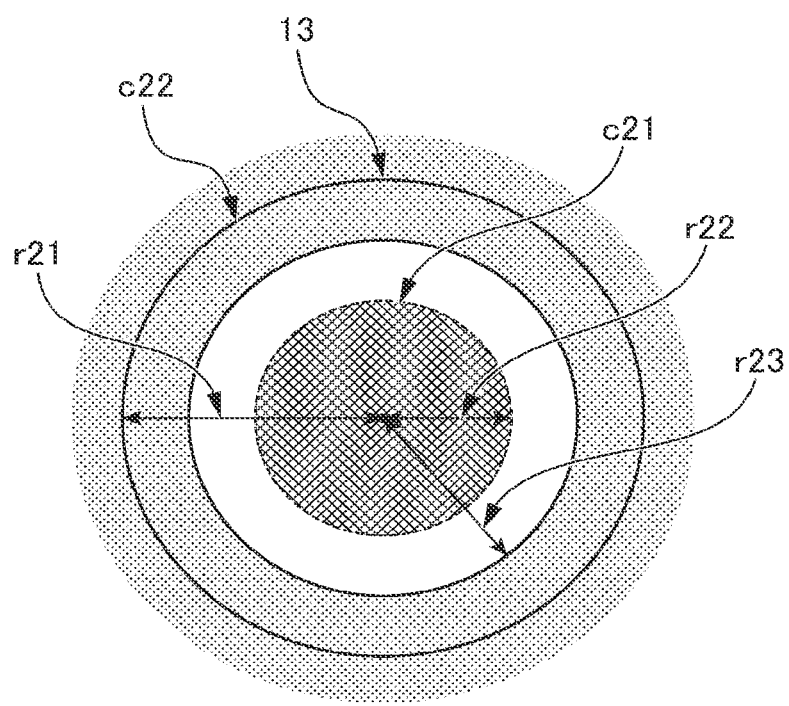
FIG. 19 is a diagram for explaining a case in which the first light intensity and the second light intensity have a second relationship.

FIG. 19 is a diagram for explaining a case in which the first light intensity and the second light intensity have a second relationship. The second relationship refers to "first light intensity"<"second light intensity". r21 represents the inner diameter of the soft portion 13. r22 represents a first radius smaller than the inner diameter of the soft portion 13. r23 represents a second radius larger than the first radius. c21 represents an inner circle having the first radius r22. c22 represents an outer circle having the second radius r23.

Furthermore, the brightest location in the inner circle c21 having the first radius r22 refers to, for example, the vicinity of the center of the inner circle c21. The brightest location in the outer circle c22 having the second radius r23 refers to, for example, the vicinity of the circumference of the outer circle c22.

That is, the vicinity of the circumference of the outer circle c22 appears brighter than the vicinity of the center of the inner circle c21. In this manner, the notification unit is configured so that the first light intensity and the second light intensity differ from each other, such that it is possible for the notification unit to notify the location in the vicinity of the center of the soft portion 13.

Here, since the light emitted from the light emitting unit 60 diffuses, when the light passes through the skin surface from the inside of the body, the transmitted light may be blurred, and the position of the soft portion 13 may become difficult to visually recognize. Therefore, it is preferable to suppress the diffusion of the light. Although details will be described later, by incorporating a light emitting unit in a cylindrical member having a reflective inner surface, the diffusion of light is suppressed, transmitted light is not blurred, and the position of the soft portion 13 (center position) is more easily visually recognized.

Furthermore, since the light emitting unit 60 has a certain emission angle, the light is diffused. However, when the installation angle of the light emitting unit 60 disposed around the soft portion 13 is sloped outward from the direction perpendicular or substantially perpendicular to the emission surface of the light, the vicinity of the center of the soft portion 13 becomes darker than the periphery of the soft portion 13. This makes it easier to visually recognize the center of the soft portion 13.

As will be described in detail later, the extracorporeal unit 20, which is an external power supply device, has a function of adjusting the amount of electric power. According to such a configuration, for example, when the light emitted from the light emitting unit 60 is too bright and the light transmitted through the skin surface overlaps, and thus the center of the soft portion 13 is difficult to visually recognize, it is possible adjust the amount of light emitted from the light emitting unit 60 so as to reduce the amount of electric power to the extent that the center of the soft portion 13 can be visually recognized. On the other hand, for example, when the light emitted from the light emitting unit 60 is too dark, the light transmitted to the skin surface is weak, and thus the center of the soft portion 13 is difficult to visually recognize, it is possible to adjust the amount of light emitted from the light emitting unit 60 so as to increase the amount of electric power to such an extent that the center of the soft portion 13 can be visually recognized.

Figure 20:
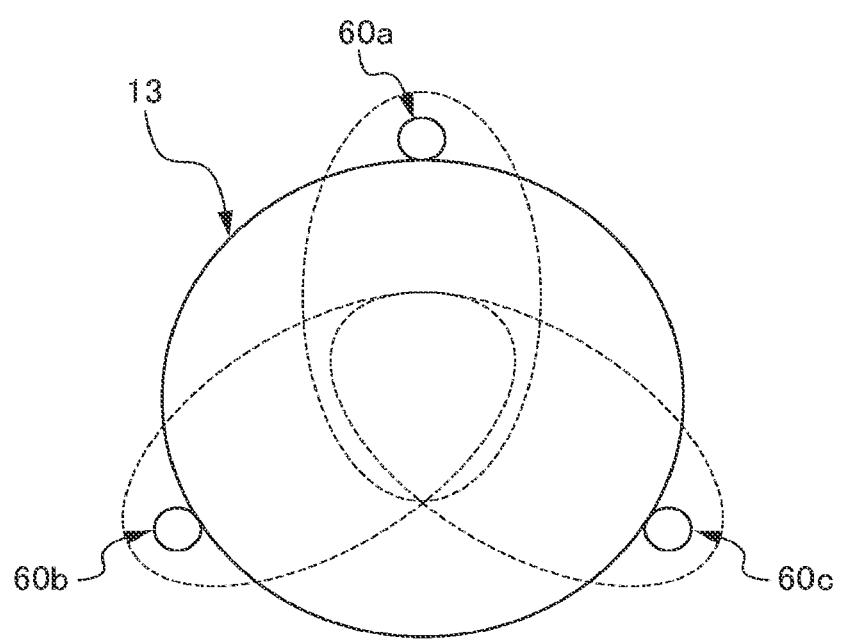
FIG. 20 is a diagram for explaining a first example in which a notification unit is configured so that the first light intensity and the second light intensity have the first relationship.

FIG. 20 is a diagram for explaining a first example in which the notification unit is configured such that the first light intensity and the second light intensity have a first relationship. FIG. 20 is a diagram schematically showing a state when the soft portion 13 is viewed from the top surface. Furthermore, FIG. 20 schematically shows a state in which the light emitting units 60a, 60b, and 60c constituting the notification unit emit light.

Figure 21:
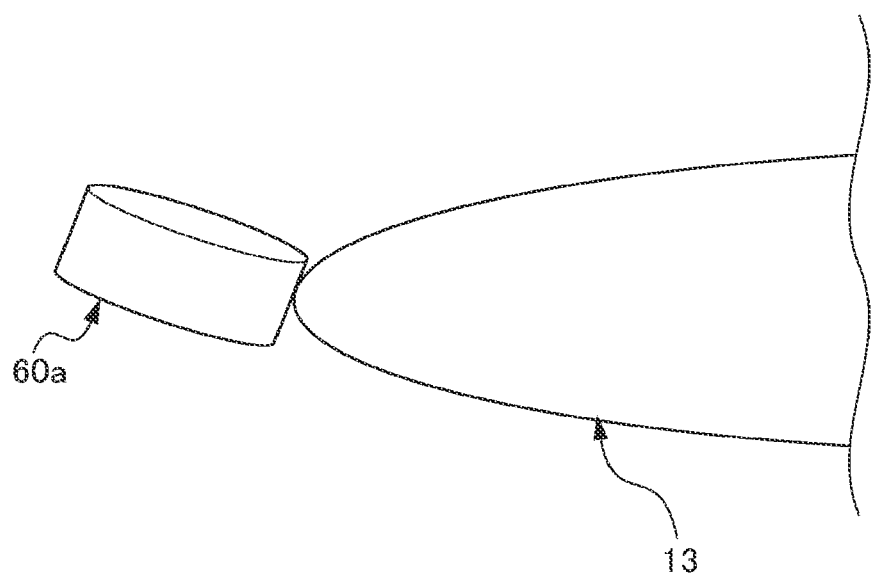
FIG. 21 is a diagram schematically showing a state in which a light emitting unit is sloped toward the center of a soft portion.

As shown in FIG. 20, the light emitting units 60a, 60b, and 60c are arranged at predetermined intervals (e.g., every 120 degrees) around the soft portion 13. FIG. 21 is a diagram schematically showing a state in which the light emitting unit 60a is sloped toward the center of the soft portion 13. It should be noted that, although only the light emitting unit 60a is shown in FIG. 21, the light emitting units 60b and 60c are also sloped toward the center of the soft portion 13. In this manner, the light emitting units 60a, 60b, and 60c are disposed so as to be sloped at a predetermined angle toward the center of the soft portion 13.

With this configuration, it is possible for the notification unit to emit light differently between the first light intensity and the second light intensity such that the vicinity of the center of the soft portion 13 is brighter than the outer periphery, and thus it is possible to notify the position of the vicinity of the center of the soft portion 13.

It should be noted that the light emitting units 60a, 60b, and 60c may emit light in different colors from each other. More specifically, for example, when the light emitted by the light emitting unit 60a is red (R), the light emitted by the light emitting unit 60b is green (G), and the light emitted by the light emitting unit 60c is blue (B), the vicinity of the center of the soft portion 13 in which each color is mixed (subtractive color mixing) is white. Therefore, it is possible to set the color (white) near the center of the soft portion 13 to be different from the color at locations other than the location near the center of the soft portion 13. The difference in colors makes it possible to notify the location in the vicinity of the soft portion 13.

Figure 22:
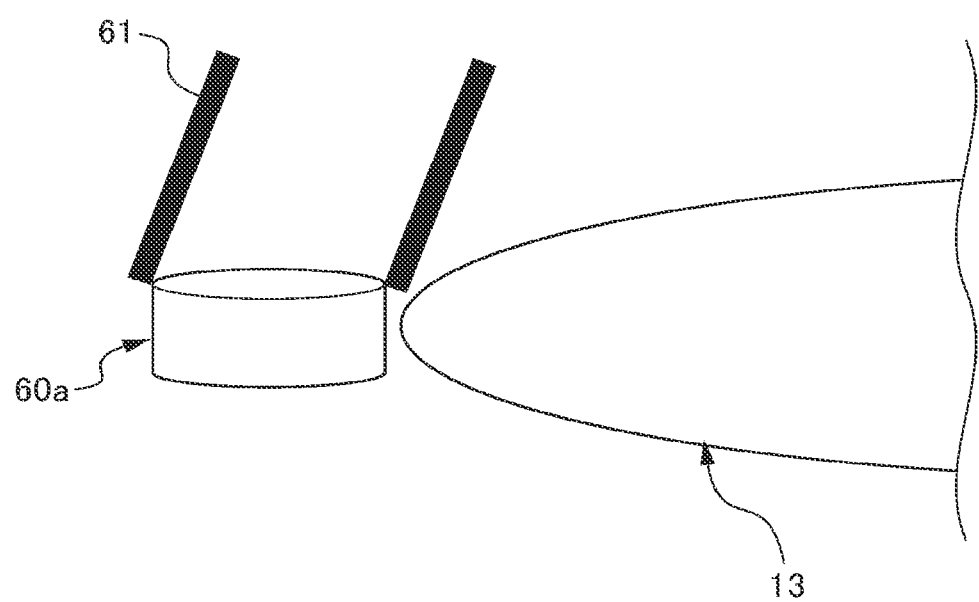
FIG. 22 is a diagram schematically showing a state in which the light emitting unit is viewed from a lateral side.

Furthermore, the light emitting units 60a, 60b, and 60c themselves may not be sloped. FIG. 22 is a diagram schematically showing a state in which the light emitting unit 60a is viewed from the lateral side. It should be noted that, although only the light emitting unit 60a is shown in FIG. 22, the light emitting units 60b and 60c have similar configurations.

For example, members 61 for preventing the diffusion of light and guiding the optical path to the center of the soft portion 13 may be provided around the light emitting unit 60. Even with such a configuration, the optical paths of the light emitting units 60a, 60b, and 60c can be concentrated at the center of the soft portion 13. Each of the members 61 may have, for example, a cylindrical shape. Furthermore, the member 61 may include a reflective member such as aluminum on the inner side thereof so as to reflect the light from the light emitting unit 60. Furthermore, the member 61 may include, for example, a lens for condensing the light emitted from the light emitting unit 60. It should be noted that the shape and structure of the member 61 are not limited to the above-described examples, and may vary.

Even with such a configuration, it is possible for the notification unit to emit light differently between the first light intensity and the second light intensity, and thus possible to notify the location in the vicinity of the center of the soft portion 13.

Figure 23:
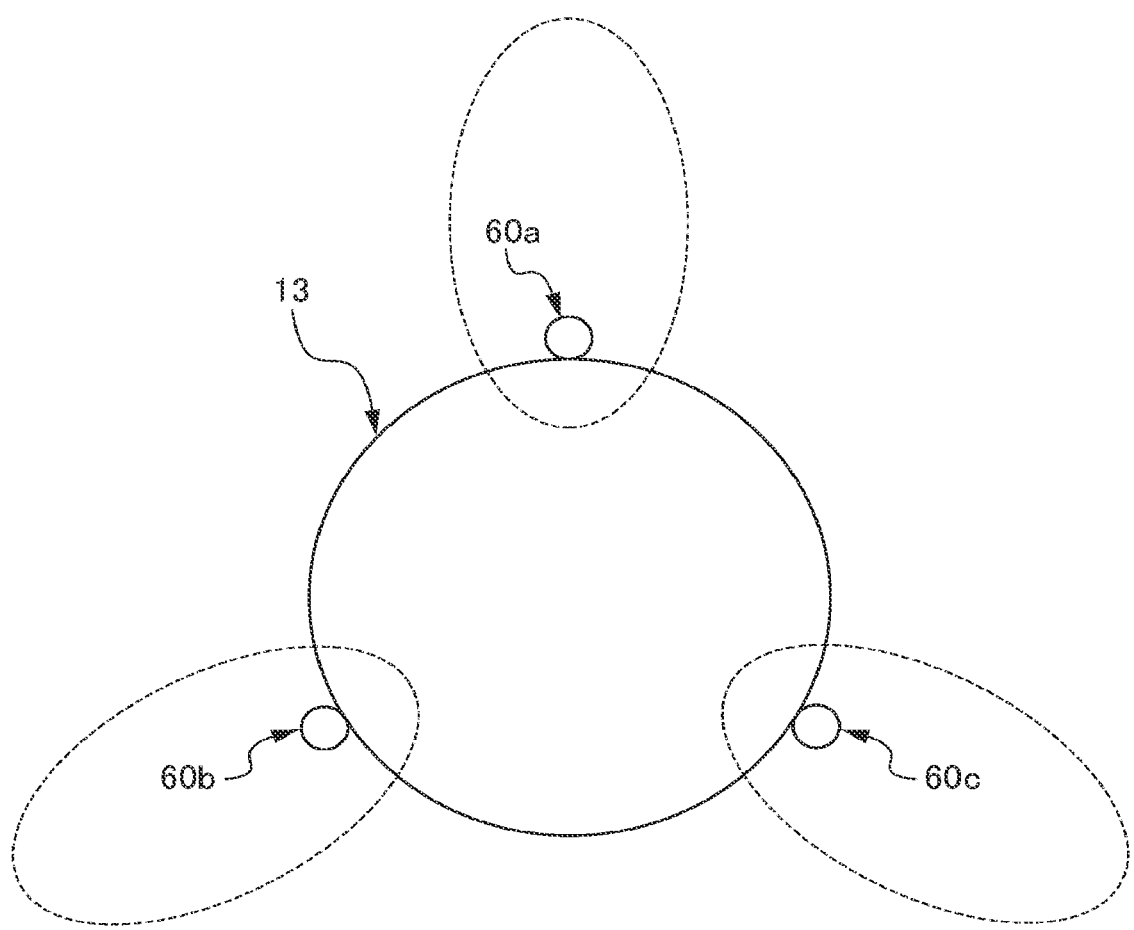
FIG. 23 is a diagram for explaining a second example in which the notification unit is configured so that the first light intensity and the second light intensity have a first relationship.

FIG. 23 is a diagram for explaining a second example in which the notification unit is configured so that the first light intensity and the second light intensity have a first relationship. FIG. 23 is a schematic view of the soft portion 13 when viewed from the upper surface. FIG. 23 schematically shows a state in which the light emitting units 60a, 60b, and 60c constituting the notification unit emit light.

Figure 24:
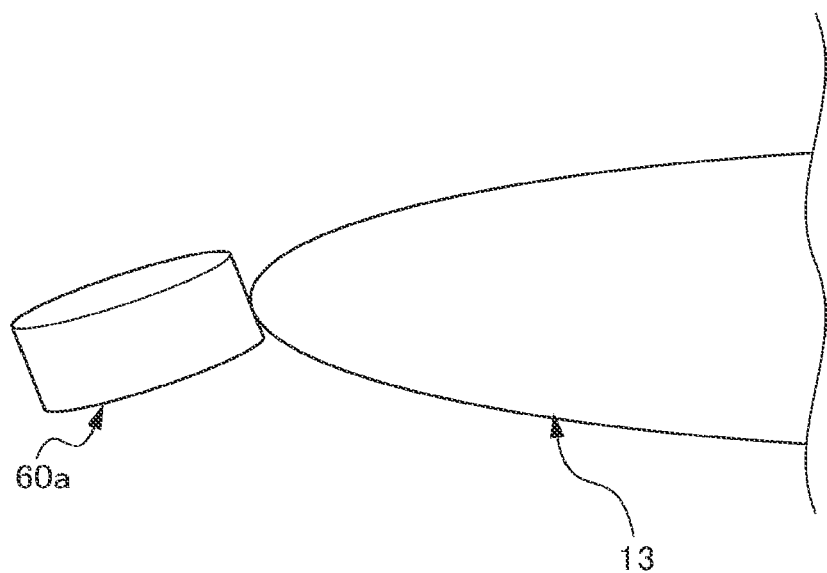
FIG. 24 is a diagram schematically showing a state in which the light emitting unit is sloped toward the outside of the soft portion.

As shown in FIG. 23, the light emitting units 60a, 60b, and 60c are arranged at predetermined intervals (e.g., every 120 degrees) around the soft portion 13. FIG. 24 is a diagram schematically showing a state in which the light emitting unit 60a is sloped toward the outside of the soft portion 13. It should be noted that, although only the light emitting unit 60a is shown in FIG. 24, the light emitting units 60b and 60c are also sloped toward the outside of the soft portion 13. In this manner, the light emitting units 60a, 60b, and 60c are disposed so as to be sloped at a predetermined angle toward the outside of the soft portion 13.

With this configuration, since it is possible to emit light differently between the first light intensity and the second light intensity so that the vicinity of the center of the soft portion 13 is darker than the outer periphery, the notification unit can notify the location in the vicinity of the center of the soft portion 13.

Figure 25:
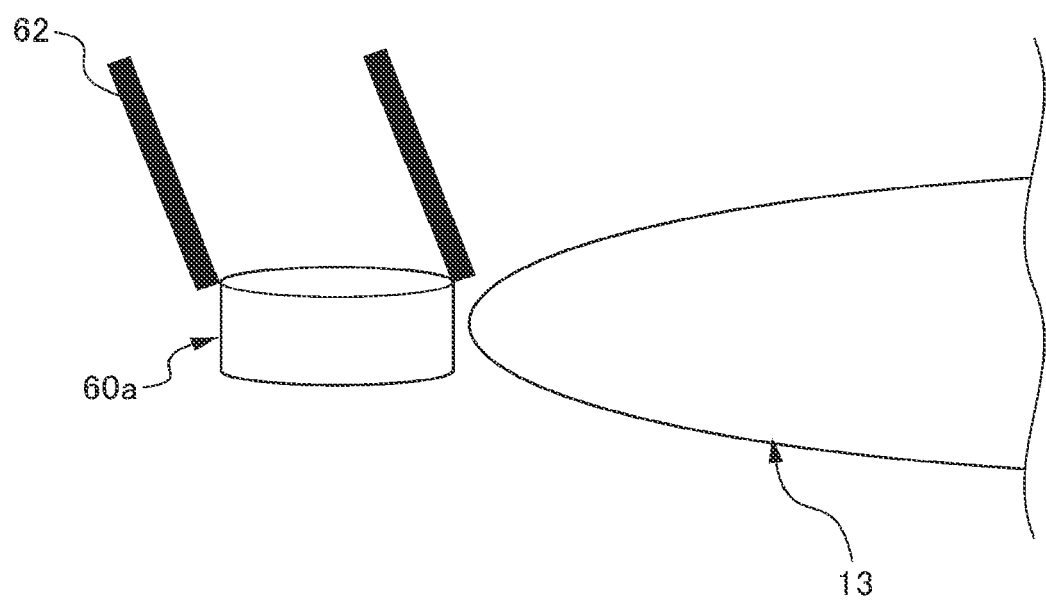
FIG. 25 is a diagram schematically showing a state in which the light emitting unit is viewed from a lateral side.

Furthermore, the light emitting units 60a, 60b, and 60c themselves may not be sloped. FIG. 25 is a diagram schematically showing a state when the light emitting unit 60 is viewed from the lateral side.

For example, members 62 for preventing the diffusion of light and guiding the optical path to the periphery of the soft portion 13 may be provided around the light emitting unit 60. Even with such a configuration, the optical paths of the light emitting units 60a, 60b, and 60c can be concentrated at the periphery of the soft portion 13. Each of the members 62 may have, for example, a cylindrical shape. Furthermore, the member 62 may include a reflective member such as aluminum on the inner side thereof so as to reflect the light from the light emitting unit 60. Furthermore, the member 62 may include, for example, a lens for condensing the light emitted from the light emitting unit 60. It should be noted that the shape and structure of the member 62 are not limited to the above-described examples, and may vary.

Even with such a configuration, it is possible for the notification unit to emit light differently between the first light intensity and the second light intensity, and thus the notification unit can notify the location in the vicinity of the center of the soft portion 13.

Figure 26:
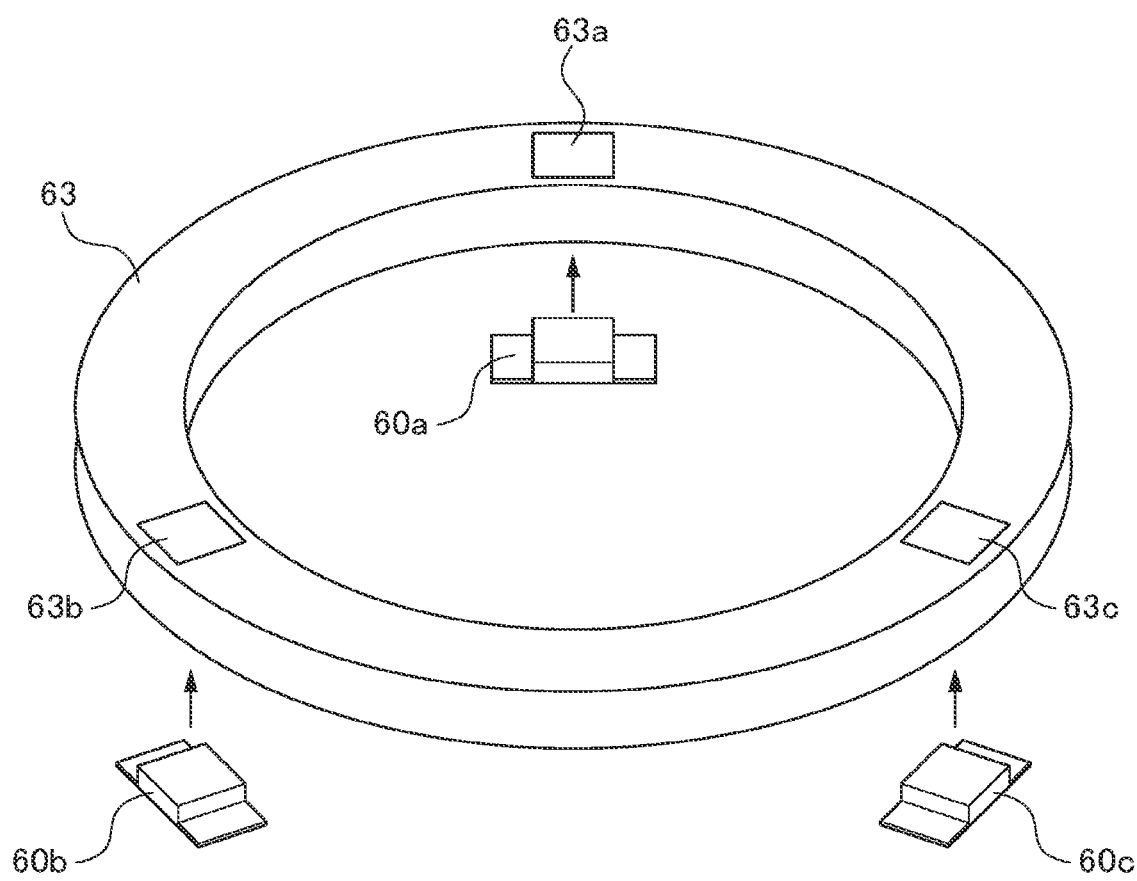
FIG. 26 is a diagram schematically showing a member in which a cylindrical hole for attaching a light emitting unit is provided.

Here, a member 63 having the functions of the members 61 and 62 will be described. FIG. 26 is a diagram schematically showing a member 63 in which cylindrical holes 63a, 63b, and 63c for attaching (embedding) the light emitting unit 60 are provided. The member 63 has an annular or substantially annular shape, and has a hole having a predetermined size provided at the center thereof. The member 63 is disposed on the body portion 11 so that the surface of the soft portion 13 is exposed from the hole. The cylindrical holes 63a, 63b, and 63c are disposed uniformly around the member 63 (for example, at 120 degrees). The light emitting unit 60a is attached to the cylindrical hole 63a. The light emitting unit 60b is attached to the cylindrical hole 63b. The light emitting unit 60c is attached to the cylindrical hole 63c.

The cylindrical holes 63a, 63b, 63c are sloped to the center side or the circumferential side of the member 63. For example, when the cylindrical holes 63a, 63b, and 63c are provided to tilt the optical path of each light emitting unit 60 in the direction that guides the optical path to the center of the soft portion 13 (toward the center of the member 63), the same effect as that obtained when the member 61 is provided can be obtained. Furthermore, for example, when the cylindrical holes 63a, 63b, and 63c are provided in a direction that guides the optical path of each light emitting unit 60 to the periphery of the soft portion 13 (on the circumferential side of the member 63), the same effect as that obtained when the member 62 is provided can be obtained.

In addition, since the cylindrical holes 63a, 63b, and 63c are uniformly provided on the circumference of the member 63, the positioning of the light emitting units 60a, 60b, and 60c can be easily performed, and the same effect as when the member 61 or 62 is provided can be achieved simply by attaching the light emitting units 60a, 60b, and 60c to the cylindrical holes 63a, 63b, and 63c, respectively.

Figure 27:
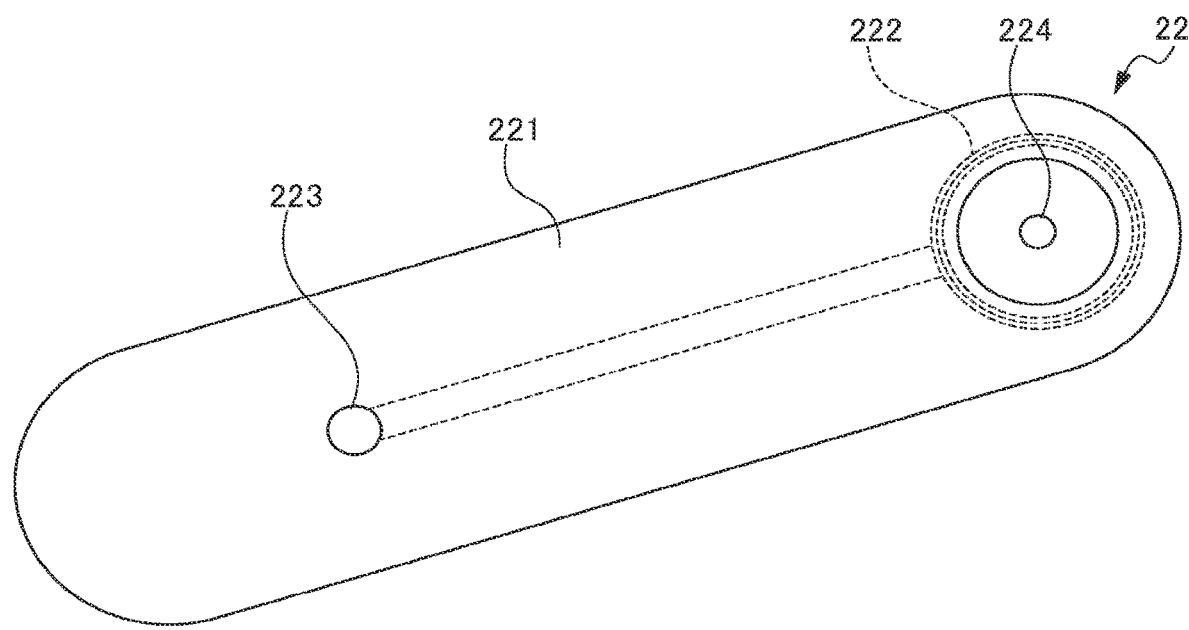
FIG. 27 is a schematic diagram showing a schematic configuration of a power transmission unit.

FIG. 27 is a schematic diagram showing a schematic configuration of the power transmission unit 22. The power transmission unit 22 has a function of transmitting power in a non-contact manner.

The power transmission unit 22 shown in FIG. 1, FIG. 2, and FIG. 27 has a plate-shaped sheet portion 221. The sheet portion 221 includes the second coil 222 on one side thereof for transmitting electric power, and has a hole 224 in the second coil 222 for insertion of an injection needle thereinto. Furthermore, the sheet portion 221 includes the second connecting portion 223 on the other side thereof. The second connecting portion 223 electrically connects the second coil 222 and the power supply unit 212 of the housing unit 21 with each other. It should be noted that it is necessary to prevent the injection needle from shifting from the soft portion 13 when the injection needle is pierced. As will be described later in detail, it is preferable that the hole 224 is slightly smaller than the soft portion 13.

The sheet portion 221 has an arc shape on both ends in the longitudinal direction. The sheet portion 221 is implemented using, for example, a nonwoven fabric or the like. Furthermore, the sheet portion 221 includes two sheets of nonwoven fabric sandwiching the second coil 222 and the second connecting portion 223. It should be noted that, in exemplary embodiment 3, a seal member provided with an attachment member, an adhesive member, or the like, which can be attached to a subject, may be provided on the back side (subject side) of the sheet portion 221. In addition, in exemplary embodiment 3, a lubricant, in place of the seal member, may be applied to the back side (the subject side) of the sheet portion 221 so as to be able to smoothly move on the body surface 101 of the subject.

The second coil 222 has an annular or substantially annular shape, and is provided on one side of the sheet portion 221 in the longitudinal direction. The second coil 222 generates a magnetic flux in response to the power inputted from the housing unit 21 via the second connecting portion 223.

The second connecting portion 223 is provided on the other side of the sheet portion 221 in the longitudinal direction, and electrically connects the power supply unit 212 of the housing unit 21 and the second coil 222. The second connecting portion 223 includes, for example, a male electrical coupler.

The hole 224 is provided in the second coil 222. For example, the hole 224 is provided at the center of the second coil 222. The hole 224 allows for the insertion and removal of the injection needle. It should be noted that the inner diameter of the second coil 222 and the diameter of the hole 224 can be appropriately changed in accordance with the diameter of the soft portion 13.

Furthermore, although details will be described later, the hole 224 is slightly larger than the diameter of the injection needle. It is preferable that the diameter of the hole 224 is equal to or less than the diameter of the injection needle+0.2 mm. By designing with such a dimension, even when the notification is made when the central detection accuracy of the second coil 222 deviates by several millimeters, it is still possible to insert the injection needle into the soft portion 13. The amount of deviation will be acceptable at less than or equal to the radius of the soft portion 13, and thus it is possible to alleviate the central detection accuracy of the coil, whereby designing becomes easy, and it is effective in terms of manufacturability and cost. Furthermore, it is also possible to extend the durability of the soft portion 13 without concentrating the location where the soft portion 13 is punctured with the injection needle at a single point.

Here, the size (diameter F) of the hole 224 will be described below; however, the diameter F of the hole 224 is considered in various ways, and thus is not limited to the following description.

Figure 28:
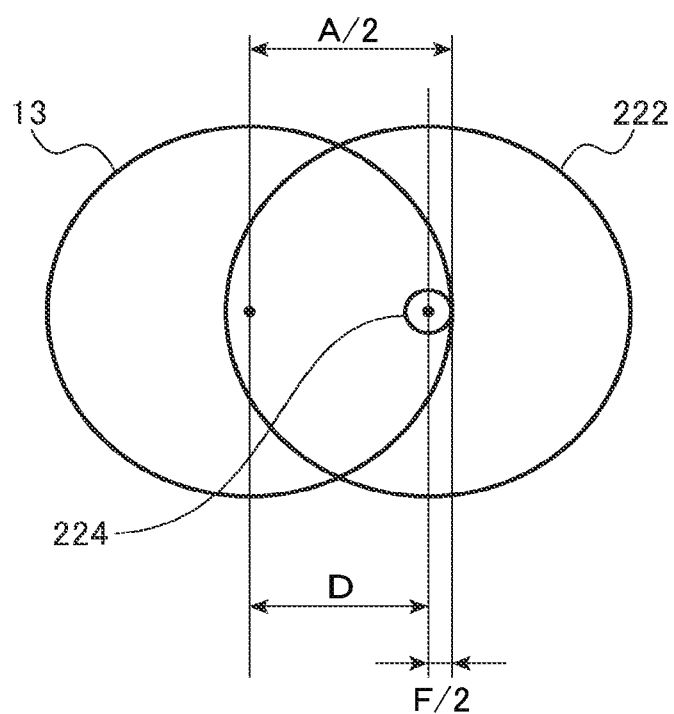
FIG. 28 is a diagram for explaining the diameter of the hole.

FIG. 28 is a diagram for explaining the diameter F of the hole 224. In FIG. 28, as an example, it is assumed that the size of the soft portion 13 and the size of the second coil 222 are substantially the same.

Based on FIG. 28, the diameter F of the hole 224 is defined by the following expression.

$$F=(A-2D) \quad (1)$$

Herein, A indicates the diameter of the soft portion 13. D indicates the distance between the center of the soft portion 13 and the center of the second coil 222 when the light emitting unit 60 can emit light. That is, the distance D shows the amount of deviation (accuracy) between the center of the second coil 222 and the center of the soft portion 13. The diameter F of the hole 224 is determined depending on the tolerable amount of deviation.

For example, the distance D can be controlled by controlling the magnitude of the magnetic flux generated from the extracorporeal unit 20G. When the magnetic flux generated from the extracorporeal unit 20 is large (hereinafter, referred to as the first configuration), the notification unit operates (emits light) by the power received by the first coil 15 even when the distance between the second coil 222 and the first coil 15 is a predetermined distance or more. In the case of the first configuration, since the notification by the notification unit can be performed at a location where the center of the second coil 222 and the center of the soft portion 13 are separated from each other, it is necessary for the diameter F of the hole 224 to be smaller than that of the second configuration to be described later.

Figure 29:
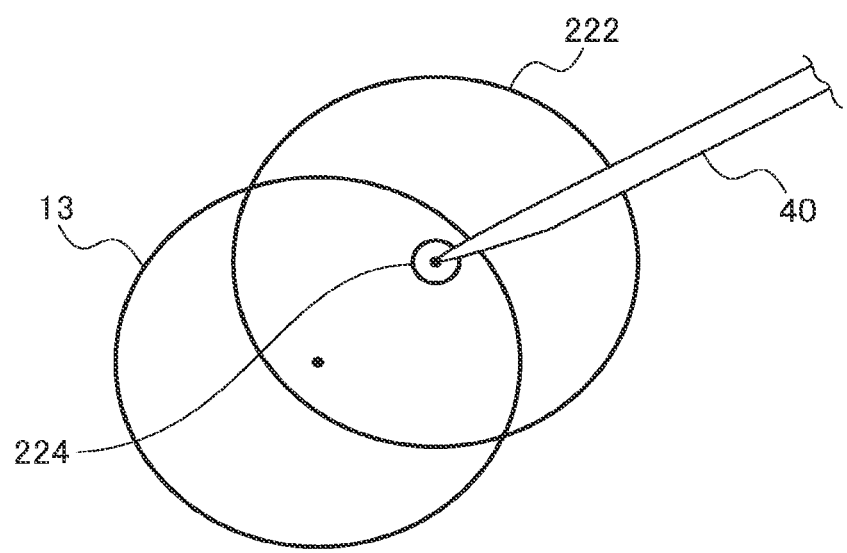
FIG. 29 is a first view for explaining the relationship between the hole and the soft portion.
Figure 30:
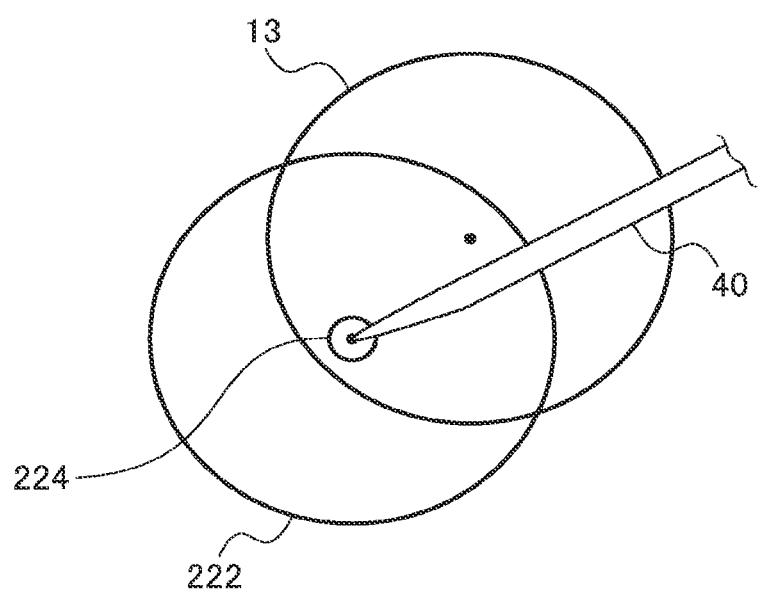
FIG. 30 is a second view for explaining the relationship between the hole and the soft portion.
Figure 31:
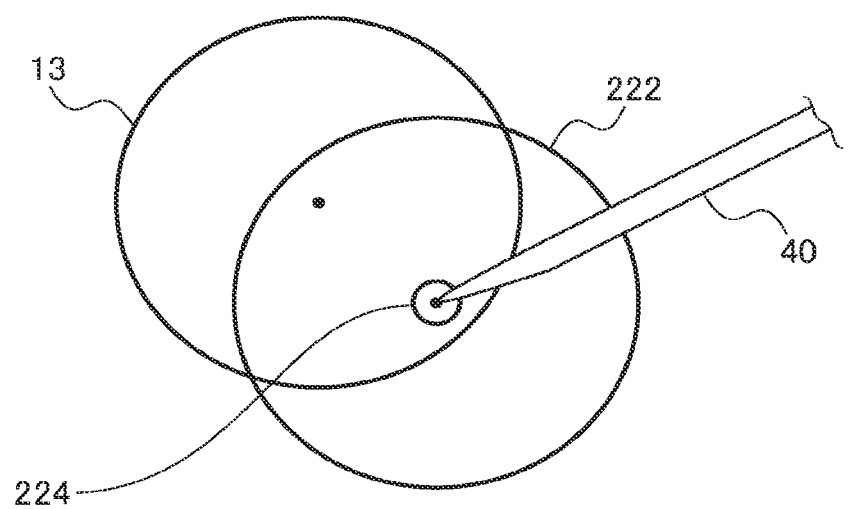
FIG. 31 is a third view for explaining the relationship between the hole and the soft portion.

FIGS. 29, 30, and 31 are diagrams for explaining the relationship between the hole 224 and the soft portion 13 in the case of the first configuration. When the inner diameter of the hole 224 is substantially the same as or slightly larger than the outer diameter of the injection needle 40 based on the expression (1), even when the center of the second coil 222 is deviated from the center of the soft portion 13, the injection needle 40 still can hit the soft portion 13 when the injection needle 40 is inserted into the hole 224. Furthermore, as shown in FIGS. 29, 30, and 31, by changing the location of the second coil 222 every time the soft portion 13 is punctured with the injection needle 40, it is possible to prevent the same location of the soft portion 13 from being punctured with the injection needle 40 many times, and thus it is possible to extend the life of the soft portion 13.

Furthermore, when the magnetic flux generated from the extracorporeal unit 20 is small (hereinafter, referred to as a second configuration), and when the distance between the second coil 222 and the first coil 15 is within the predetermined distance, the notification unit operates (emits light) by the power received by the first coil 15. In the case of the second configuration, since the notification is performed by the notification unit at a location where the center of the second coil 222 and the center of the soft portion 13 are close to each other, it is possible to make the diameter F of the hole 224 larger than that of the first configuration described above.

More specifically, the input unit 214 inputs a value based on a user operation to the control unit 219. The control unit 219 controls the power supply unit 212 based on the value inputted from the input unit 214. The power supply unit 212 supplies power to the second coil 222 based on the control of the control unit 219.

For example, when it is desired to generate a large magnetic flux from the extracorporeal unit 20, the user inputs the value V1 to the control unit 219 using the input unit 214. In addition, when it is desired to generate a small magnetic flux from the extracorporeal unit 20, the user inputs the value V2 to the control unit 219 using the input unit 214. Here, the relationship of value V1>value V2 is satisfied. It should be noted that, in the above description, the magnitude of the magnetic flux has been described in two stages; however, the present invention is not limited thereto, and the magnitude of the magnetic flux may be controlled in three stages or more.

Here, when the diameter F of the hole 224 is made slightly smaller than the diameter A of the soft portion 13, the diameter F of the hole 224 is determined based on the expression (2).

$$F<(A-2D) \quad (2)$$

By determining the diameter F of the hole 224 based on the expression (2), a medical doctor or a nurse as a user can puncture the soft portion 13 with an injection needle so as not to deviate from the soft portion 13.

Although various shapes and sizes are applied to the medical instrument 10, for example, if the diameter A of the soft portion 13 is determined as 8.0 mm and the diameter F of the hole 224 is determined as 1.1 mm, the distance D is obtained from the expression (2) as follows. Here, the diameter F of the hole 224 is determined as the diameter of the injection needle. Furthermore, the diameter F of the hole 224 (the diameter of the injection needle) is determined to have the upper limit of SUS304, nominal 19G (outer diameter (mm): 1.08±0.02).

$$D<(8.0-1.1)/2=3.45 \text{ mm} \quad (3)$$

Here, a case of determining the distance D large, and a case of determining the distance D small will be described. In the case of determining the distance D large, it is possible for the notification unit to notify the position of the soft portion 13 even when the center of the second coil 222 and the center of the soft portion 13 (strictly, the first coil 15) are separated. In this manner, when the distance D is determined to be large, it is possible for a medical doctor or a nurse as a user to know the position of the soft portion 13 by a simple procedure.

On the other hand, when the distance D is determined to be small, it is possible for the notification unit to notify the position of the soft portion 13 by bringing the center of the second coil 222 to some extent close to the center of the soft portion 13 (strictly, the first coil 15).

In this manner, when the distance D is determined to be large, it is possible for the diameter F of the hole 224 to be larger as compared with the case where the distance D is determined to be small, such that a medical doctor or a nurse as a user can select a location where the injection needle is to be inserted, and thus it is possible to prevent the same location of the soft portion 13 from being punctured many times with the injection needle, whereby the life of the soft portion 13 can be extended.

In addition, the hole 224 may have a diameter as large as or larger than the diameter of the injection needle in order to pass through the injection needle. It should be noted that, when the injection needle is designed to penetrate the sheet portion 221, it is not necessary to provide the hole 224 in the sheet portion 221. In such a configuration, it will suffice if a mark indicating a location for the puncture of the injection needle is provided on the sheet portion 221 (for example, a location corresponding to the center of the second coil 222).

Furthermore, by providing the diameter F of the hole 224 based on the expression (4), it is possible to puncture the soft portion 13 with the injection needle so as not to deviate from the soft portion 13 in a state in which the center of the soft portion 13 is located within the region where the hole 224 is provided.

$$F > 2D \quad (4)$$

Furthermore, by providing the diameter F of the hole 224 based on the expression (5), it is possible to puncture the soft portion 13 with the injection needle so as not to deviate from the soft portion 13 in a state in which the center of the soft portion 13 is located outside the region where the hole 224 is provided.

$$F < 2D \quad (5)$$

By providing the diameter F of the hole 224 based on the expression (2), (4) or (5) as described above, it is possible to puncture the soft portion 13 with the injection needle so as not to deviate from the soft portion 13. The diameter F of the hole 224 is not limited to the expressions (2), (4), and (5).

While some of the exemplary embodiments of the present application have been described in detail based on the drawings, these are illustrative, and it is possible to implement the present invention in other forms which have been subjected to various modifications and improvements based on the knowledge of those skilled in the art, including the aspects described in the section of disclosure of the present invention.

EXPLANATION OF REFERENCE NUMERALS 1, 1D, 1G medical device
10, 10D, 10G medical instrument
11 body portion
12 medicinal solution container
12a opening
13 soft portion
14 catheter
15 first coil
16 power receiving circuit
17 first communication unit
20, 20D, 20G extracorporeal unit
21 housing unit
22 power transmission unit
40 injection needle
60 light emitting unit
70 first coil
100 living body
101 body surface
102 subject
211 first connecting portion
212 power supply unit
213 second communication unit
214 input unit
215 recording unit
216 output unit
217 display unit
218 light emitting unit
219 control unit
221 sheet portion
222, 230 second coil
223 second connecting portion
224 hole

The invention claimed is:

1. A medical device comprising:
a power transmission unit including a second coil that transmits power in a non-contact manner;
a power receiving unit including a first coil that receives the power transmitted from the power transmission unit; and
an implantable medical instrument for use in a body, the implantable medical instrument including the power receiving unit,
the implantable medical instrument including:
a soft portion for insertion of an injection needle, and
a notification unit including a plurality of light emitting units,
wherein the plurality of light emitting units is arranged along an outer edge of the soft portion,
the notification unit is configured to notify a position of the soft portion by emitting light from the plurality of light emitting units using power received by the power receiving unit when
a relative positional relationship between the second coil constituting the power transmission unit and the first coil constituting the power receiving unit has reached a predetermined state along with a movement of the power transmission unit, and
the plurality of light emitting units is configured to emit light toward a center or an outside of the soft portion so as to allow a light intensity toward the center of the soft portion and a light intensity toward the outside of the soft portion to differ from each other.

2. The medical device according to claim 1, wherein the power receiving unit includes a plurality of power receiving units, and
the plurality of light emitting units each emit light using power received by a corresponding one of the plurality of power receiving units connected thereto.

3. The medical device according to claim 1, wherein the plurality of light emitting units share the power receiving unit, and emit light using the power received by the power receiving unit.

4. The medical device according to claim 1, wherein the plurality of light emitting units is configured to allow the light intensity toward the outside of the soft portion to be greater than the light intensity toward the center of the soft portion.

5. The medical device according to claim 1, wherein the power transmission unit includes a plate-shaped sheet portion,
the plate-shaped sheet portion includes a second coil that transmits the power, and has a hole in the second coil for insertion of an injection needle thereinto, and
a diameter F of the hole is defined by the following expression, $$F < (A - 2D)$$

wherein

A indicates a diameter of the soft portion, and

D indicates a distance between the center of the soft portion and a center of the second coil when the light emitting unit can emit light.

6. An extracorporeal unit that detects a predetermined location of an implantable medical instrument for use in a body including a power receiving unit that receives power transmitted from outside in a non-contact manner, a soft portion for insertion of an injection needle, and a notification unit including a plurality of light emitting units, the extracorporeal unit comprising a power transmission unit including a second coil that transmits power in a non-contact manner, wherein the plurality of light emitting units is arranged along an outer edge of the soft portion, the notification unit is configured to notify a position of the soft portion by emitting light from the plurality of light emitting units using power received by the power receiving unit when a relative positional relationship between the power transmission unit and the power receiving unit has reached a predetermined state along with a movement of the power transmission unit, and the plurality of light emitting units is configured to emit light toward a center or an outside of the soft portion so as to allow a light intensity toward the center of the soft portion and a light intensity toward the outside of the soft portion to differ from each other, the power transmission unit includes a plate-shaped sheet portion, the plate-shaped sheet portion includes the second coil that transmits the power, and has a hole in the second coil for insertion of an injection needle thereinto, and a diameter F of the hole is defined by the following expression, $$F<(A-2D)$$

wherein

A indicates a diameter of the soft portion, and

D indicates a distance between the center of the soft portion and a center of the second coil when the light emitting unit can emit light.

7. A power transmission sheet attachable to and detachable from an extracorporeal unit that detects a predetermined location of an implantable medical instrument for use in a body including a power receiving unit that receives power transmitted from outside in a non-contact manner, a soft portion for insertion of an injection needle, and a notification unit including a plurality of light emitting units, wherein the plurality of light emitting units is arranged along an outer edge of the soft portion, the notification unit is configured to notify a position of the soft portion by emitting light from the plurality of light emitting units using power received by the power receiving unit when a relative positional relationship between the power transmission sheet and the power receiving unit has reached a predetermined state along with a movement of the power transmission sheet, and the plurality of light emitting units is configured to emit light toward a center or an outside of the soft portion so as to allow a light intensity toward the center of the soft portion and a light intensity toward the outside of the soft portion to differ from each other, the power transmission sheet including a plate-shaped sheet portion, the plate-shaped sheet portion includes a second coil that transmits the power, and has a hole in the second coil for insertion of an injection needle thereinto, and a diameter F of the hole is defined by the following expression, $$F<(A-2D)$$

wherein

A indicates a diameter of the soft portion, and

D indicates a distance between the center of the soft portion and a center of the second coil when the light emitting unit can emit light.

8. An implantable medical instrument for use in a body, comprising:

a power receiving unit including a first coil that receives power transmitted from a power transmission unit of an extracorporeal unit in a non-contact manner a soft portion for insertion of an injection needle, and;

a notification unit including a plurality of light emitting units, wherein the plurality of light emitting units is arranged along an outer edge of the soft portion, the notification unit is configured to notify a position of the soft portion by emitting light from the plurality of light emitting units using power received by the power receiving unit when a relative positional relationship between the power transmission unit and the power receiving unit has reached a predetermined state along with a movement of the power transmission unit, and the plurality of light emitting units is configured to emit light toward a center or an outside of the soft portion so as to allow a light intensity toward the center of the soft portion and a light intensity toward the outside of the soft portion to differ from each other.

* * * * *